United States Patent [19]
Hubschwerlen et al.

[11] Patent Number: 5,811,419
[45] Date of Patent: Sep. 22, 1998

[54] ISOOXACEPHEM-DERIVATIVES

[75] Inventors: Christian Hubschwerlen, Durmenach; Jean-Luc Specklin, Kembs-Loechle, both of France

[73] Assignee: Hoffmann-La Roche Inc., Nutley, N.J.

[21] Appl. No.: 768,369

[22] Filed: Dec. 17, 1996

[30] Foreign Application Priority Data

Jan. 16, 1996 [EP] European Pat. Off. ............. 96100538

[51] Int. Cl.$^6$ ...................... A61K 31/535; C07D 507/08
[52] U.S. Cl. ............................................ 514/210; 540/300
[58] Field of Search ............................. 540/300; 514/210

[56] References Cited

U.S. PATENT DOCUMENTS

| | | | |
|---|---|---|---|
| 3,971,778 | 7/1976 | Cook et al. | 260/243 C |
| 4,399,131 | 8/1983 | Dürckheimer et al. | 424/246 |
| 4,404,373 | 9/1983 | Iwanami et al. | 544/21 |
| 5,523,400 | 6/1996 | Wei et al. | 514/202 |

FOREIGN PATENT DOCUMENTS

| | | |
|---|---|---|
| 866 038 | 10/1978 | Belgium . |
| 867 994 | 12/1978 | Belgium . |
| 0 313 081 | 4/1989 | European Pat. Off. . |
| 0 405 217 | 1/1991 | European Pat. Off. . |
| 0 620 225 | 10/1994 | European Pat. Off. . |
| 93/15085 | 8/1993 | WIPO . |
| 96/26943 | 9/1996 | WIPO . |

OTHER PUBLICATIONS

Doyle, Terrence W., et al., *Canadian Journal of Chemistry*, 58 (23):2508–23 (1980).

Mastalerz, Harold, et al., *Journal of Medicinal Chemistry*, 31(6);1190–6 (1988).

Tsubouchi, Hidetsugu, et al., *Journal of Medicinal Chemistry*, 38(12):2152–7 (1995).

Derwent Abstract No. AN 91–008617/02 incomplete citation no year.

Green, T., *Protective Groups in Organic Synthesis*, Chapter 5, John Wiley and Sons, Inc., pp. 152–192 (1981).

Green, T., *Protective Groups in Organic Synthesis*, Chapter 7, John Wiley and Sons, Inc. pp. 218–287 (1981).

*Primary Examiner*—John M. Ford
*Attorney, Agent, or Firm*—George W. Johnston; Dennis P. Tramaloni; Alan P. Kass

[57] ABSTRACT

Compounds of formula I

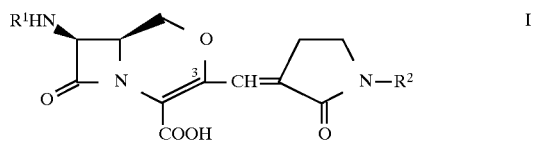

wherein $R^1$ is hydrogen or an acyl group derived from a carboxylic acid;

$R^2$ is hydrogen, hydroxy, lower alkyl, cycloalkyl, lower alkoxy, lower alkenyl, cycloalkenyl, lower alkynyl, aryl-lower alkyl, aryl, aryloxy, aryl-lower alkoxy or a heterocyclic ring; the lower alkyl, cycloalkyl, lower alkoxy, lower alkenyl, cycloalkenyl, lower alkynyl, aryl-lower alkyl, aryl, aryloxy, aryl-lower alkoxy and the heterocyclic ring being unsubstituted or substituted with at least one group selected from carboxy, amino, nitro, cyano, lower alkyl, lower alkoxy, hydroxy, halogen, —$CONR^{21}R^{22}$, —$N(R^{22})COOR^{23}$, $R^{22}CO$—, $R^{22}OCO$— or $R^{22}COO$—, wherein $R^{21}$ is hydrogen, lower alkyl, or cycloalkyl; $R^{22}$ is hydrogen or lower alkyl; $R^{23}$ is lower alkyl, lower alkenyl or a carboxylic acid protecting group;

as well as readily hydrolyzable esters thereof, pharmaceutically acceptable salts of said compounds and hydrates of the compounds of formula I and of their esters and salts as provided for herein. The invention also relates to pharmaceutical compositions and methods of use of these compounds.

52 Claims, No Drawings

ISOOXACEPHEM-DERIVATIVES

The present invention relates to compounds of formula I

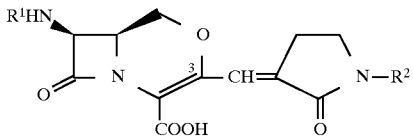

wherein
$R^1$ is hydrogen or an acyl group derived from a carboxylic acid;
$R^2$ is hydrogen, hydroxy, lower alkyl, cycloalkyl, lower alkoxy, lower alkenyl, cycloalkenyl, lower alkynyl, aryl-lower alkyl, aryl, aryloxy, aryl-lower alkoxy or a heterocyclic ring; the lower alkyl, cycloalkyl, lower alkoxy, lower alkenyl, cycloalkenyl, lower alkynyl, aryl-lower alkyl, aryl, aryloxy, aryl-lower alkoxy and the heterocyclic ring being unsubstituted or substituted with at least one group selected from carboxy, amino, nitro, cyano, lower alkyl, lower alkoxy, hydroxy, halogen, $—CONR^{21}R^{22}$, $—N(R^{22})COOR^{23}$, $R^{22}CO—$, $R^{22}OCO—$ or $R^{22}COO—$, wherein $R^{21}$ is hydrogen, lower alkyl, or cycloalkyl; $R^{22}$ is hydrogen or lower alkyl; $R^{23}$ is lower alkyl, lower alkenyl or a carboxylic acid protecting group;
as well as readily hydrolyzable esters thereof, pharmaceutically acceptable salts of said compounds and hydrates of the compounds of formula I and of their esters and salts.

The invention also relates to pharmaceutical compositions and methods of use of the above compounds.

In the above compounds of formula I the substituent in position 3 can be present in the E-form having the formula Ia

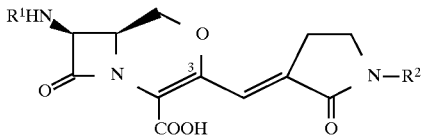

or in the Z-form having the formula Ib

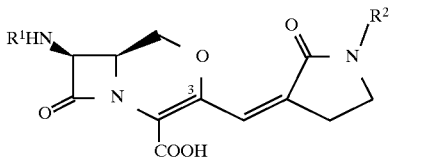

The term "acyl group derived from a carboxylic acid" used in conjunction with $R^1$ herein refers to all organic radicals derived from an organic carboxylic acid by removal of the hydroxyl group. Although the group $R^1$ may be any one of many acyl radicals, certain acyl groups are preferred, as described below.

Exemplary acyl groups are those groups which can be used to acylate β-lactam antibiotics, including 6-aminopenicillanic acid and derivatives and 7-aminocephalosphoranic acid and derivatives; see, for example, Cephalosporins and Penicillins, edited by Flynn, Academic Press (1972), Belgian Patent No. 866,038, published Oct. 17, 1978, Belgian Patent No. 867,994, published Dec. 11, 1978 and U.S. Pat. No. 3,971,778, issued Jul. 27, 1976.

The following list of acyl groups a to g for the residue $R^1$ of formula I is presented to further exemplify the term "acyl", without intending to limit that term to only those groups set forth.

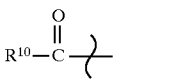 a

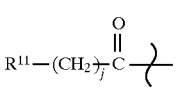 b

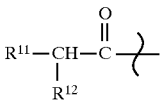 c

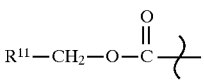 d

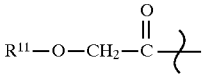 e

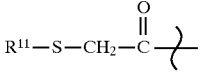 f

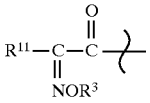 g wherein
j is 0, 1, 2 or 3;
$R^3$ is hydrogen, lower alkyl, cycloalkyl, carbamoyl-lower alkyl, aryl-lower alkyl;
$R^{10}$ is hydrogen, lower alkyl, cycloalkyl, lower alkoxy, lower alkenyl or cycloalkenyl, the lower alkyl group or the lower alkenyl group being optionally substituted with at least one group selected from halogen, cyano, nitro, amino, mercapto, alkylthio or cyano-methylthio;
$R^{11}$ is aryl which is unsubstituted or substituted with at least one group selected from halogen, hydroxy, nitro, amino, cyano, carboxy, lower alkyl, lower alkoxy, carbamoyl, trifluoromethyl or aminomethyl; a heterocyclic ring which is unsubstituted or substituted with at least one group selected from halogen, hydroxy, nitro, amino, cyano, carboxy, lower alkyl, lower alkoxy, carbamoyl, trifluoromethyl, aminomethyl or substituted with optionally substituted phenyl or fused together with a benzene ring;
$R^{12}$ is amino, acylamino, hydroxy, sulfato, a carboxyl salt, protected carboxy or azido.

The aliphatic acyl groups used in conjunction with $R^1$ have the formula a, wherein $R^{10}$ is as defined above.

Preferred aliphatic acyl groups are those wherein $R^1$ is lower alkanoyl, particularly acetyl.

The aromatic or heteroaromatic acyl groups used in conjunction with $R^1$ have the formulae b to f, wherein j, $R^{11}$ and $R^{12}$ are as defined above.

The aryl group in the residue $R^{11}$ is preferably phenyl.

Examples for heteroaromatic acyl groups suitable for the purposes of the present invention include those groups of the above formulae b to f wherein $R^{11}$ is isoxazolyl, 2,6-dichlorophenyl-5-methyl-isoxazolyl, tetrazolyl, 1-methyltetrazolyl, 2-amino-4-thiazolyl, 2-amino-5-halo-4-thiazolyl, 4-aminopyridin-2-yl, 2-amino-1,3,4-thiadiazol-5-yl, 5-amino-1,2,4-thiadiazol-3-yl, 2-thienyl, 2-furanyl, 4-pyridinyl, 2,6-dichloro-4-pyridinyl or 2-amino-4-benzothiazolyl.

Preferred heteroaromatic acyl groups are those wherein $R^1$ is a residue of the formula b, particularly 2,6-dichlorophenyl-5-methyl-isoxazol-4-yl-carbonyl. Also preferred are heteroaromatic acyl groups wherein $R^1$ is a residue of the formula f, particularly 1-methyl-tetrazol-5-yl-sulfanyl-acetyl.

The oxyimino-acyl groups used in conjunction with $R^1$ have the formula g, wherein $R^3$ and $R^{11}$ are as defined above.

Preferred are oxyimino-acyl groups of the formula g wherein $R^{11}$ is a heterocyclic ring which is unsubstituted or substituted with at least one group selected from halogen, hydroxy, nitro, amino, cyano, carboxy, lower alkyl, lower alkoxy, carbamoyl, trifluoromethyl or aminomethyl or substituted with optionally substituted phenyl or fused together with a benzene ring. The heterocyclic ring is preferably the thiazolyl ring or the thiadiazolyl ring.

Most preferred is an amino substituted thiazolyl ring. The thus obtained subgroup of compounds of the invention consists of compounds of the formula II

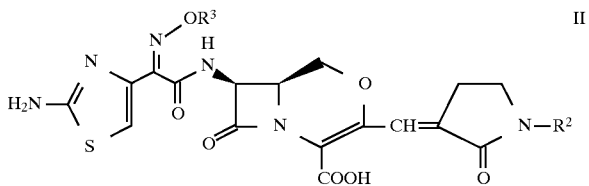

wherein $R^2$ is as defined under formula I and $R^3$ is as defined above.

In formula II $R^3$ is preferably hydrogen, carbamoyl-lower alkyl or cycloalkyl, particularly hydrogen, carbamoyl-methyl or cyclopentyl.

Preferred compounds of formula II are such where $R^2$ is lower alkyl, cycloalkyl, aryl-lower alkyl, aryl or a heterocyclic ring, the lower alkyl, aryl-lower alkyl, aryl and the heterocyclic ring being unsubstituted or substituted with at least one group selected from halogen, hydroxy, amino, nitro, cyano, lower alkyl or lower alkoxy.

Most preferred compounds of formula II are such wherein $R^2$ is isobutyl, 2,2,2-trifluoroethyl, cyclopropyl, phenyl, 3-nitrophenyl, 4-hydroxyphenyl, 2-fluorophenyl, 2-methoxyphenyl, 4-nitrobenzyl, pyridinyl, N-methyl-pyridinium-2yl or 5-methyl-isoxazolyl.

As used herein, the term "lower alkyl" refers to both straight and branched chain saturated hydrocarbon groups having 1 to 8, preferably 1 to 4 carbon atoms, for example, methyl, ethyl, n-propyl, isopropyl, tertiary butyl and the like.

By the term "cycloalkyl" is meant a 3–7 membered saturated carbocyclic ring e.g., cyclopropyl, cyclobutyl, cyclopentyl, cyclohexyl and the like.

The term "lower alkoxy" refers to alkoxy groups in the sense of the above description of the term lower alkyl. Examples include methoxy, ethoxy, n-propoxy and the like.

As used herein, "lower alkenyl" refers to an unsubstituted or substituted hydrocarbon chain radical having from 2 to 8 carbon atoms, preferably from 2 to 4 carbon atoms, and having at least one olefinic double bond, e.g. allyl, vinyl and the like.

As used herein, "cycloalkenyl" refers to a carbocyclic ring having at least one olefinic double bond.

As used herein, "lower alkynyl" refers to an unsubstituted or substituted hydrocarbon chain radical having from 2 to 8 carbon atoms, preferably 2 to 4 carbon atoms, and having at least one olefinic triple bond.

The term "halogen" used herein refers to all four forms, that is chlorine or chloro; bromine or bromo; iodine or iodo; and fluorine or fluoro.

By the term "aryl" is meant a radical derived from an aromatic hydrocarbon by the elimination of one atom of hydrogen and can be substituted or unsubstituted. The aromatic hydrocarbon can be mononuclear or polynuclear. Examples of aryl radicals of the mononuclear type include phenyl, tolyl, xylyl, mesityl, cumenyl, and the like. Examples of aryl radicals of the polynuclear type include naphthyl, anthryl, phenanthryl, and the like. The aryl group can have at least one substituent selected from, as for example, halogen, hydroxy, cyano, carboxy, carbamoyl, nitro, amino, aminomethyl, lower alkyl, lower alkoxy or trifluoromethyl. Examples include 2-fluorophenyl, 3-nitrophenyl, 4-nitrophenyl, 4-methoxyphenyl, 4-hydroxyphenyl and the like.

By the term "aryl-lower alkyl" is meant a lower alkyl group containing an aryl group as for example benzyl.

As used herein, "aryloxy" is an oxygen radical having an aryl substituent (i.e., —O-aryl).

As used herein, "aryl-lower alkoxy" is an oxygen radical having an aryl-lower alkyl substituent. (i.e., —O-lower-alkyl-aryl).

As used herein, "heterocyclic ring" refers to an unsaturated or saturated, unsubstituted or substituted 5-, 6-, or 7-membered heterocyclic ring containing at least one hetero atom selected from the group consisting of oxygen, nitrogen, or sulfur. Exemplary heterocyclic rings include, but are not limited to, for example, the following groups: pyridyl, pyrazinyl, piperidyl, piperidino, N-oxido-pyridyl, pyrimidyl, piperazinyl, pyrrolidinyl, pyridazinyl, N-oxide-pyridazinyl, pyrazolyl, triazinyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl, thienyl, furyl, hexamethyleneiminyl, oxepanyl, 1H-azepinyl, thiophenyl, tetrahydrothiophenyl, 3H-1,2,3-oxathiazolyl, 1,2,3-oxadiazolyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, oxazolidinyl, tetrahydrothienyl, etc., and others. Substituents for the heterocyclic ring include lower-alkyl, lower-alkoxy, halogen, trifluoromethyl, trichloroethyl, amino, nitro, cyano, mercapto, hydroxy, carboxy, carbamoyl, $—CONR^{21}R^{22}$, $—N(R^{22})COOR^{23}$, $R^{22}CO—$, $R^{22}OCO—$, or $R^{22}COO—$, wherein $R^{21}$ is hydrogen, lower alkyl, or cycloalkyl; $R^{22}$ is hydrogen or lower alkyl; and $R^{23}$ is lower alkyl, lower alkenyl, or a carboxylic acid protecting group. Preferred examples of substituted heterocyclic rings include 5-methyl-isoxazol-3-yl, N-methyl-pyridinium-2yl, 1-methyl-tetrazolyl and the like.

The heterocyclic ring can also be substituted by an optionally substituted phenyl ring such as 2,6-dichlorophenyl. Preferred is 2,6-dichlorophenyl-5-methyl-isoxazolyl.

A further substituent is oxo, such as in 2-oxo-oxazolidin-3-yl, 1,1-dioxo-tetrahydrothien-3-yl.

The heterocyclic ring can also be fused together with a benzene ring.

By the term "substituted phenyl" is meant phenyl mono or di-substituted.

As used herein pharmaceutically acceptable salts useful in this invention include salts derived from metals, the ammonium salt, quaternary ammonium salts derived from organic bases and amino acid salts. Examples of preferred metal salts are those derived from the alkali metals, for example, lithium ($Li^+$), sodium ($Na^+$) and potassium ($K^+$), and from the alkaline earth metals, for example, calcium ($Ca^{++}$) and magnesium ($Mg^{++}$), although cationic forms of other metals, such as iron ($Fe^{++}$ or $Fe^{+++}$), aluminum ($Al^{+++}$), and zinc ($Zn^{++}$) are within the scope of this invention. Examples of quaternary ammonium salts derived from organic bases include tetramethylammonium ($N^+(CH_3)_4$), tetraethylammonium ($N^+(CH_2CH_3)_4$), benzyltrimethylammonium ($N^+(C_6H_5CH_2)(CH_3)_3$), phenyltriethylammonium ($N^+(C_6H_5)(CH_2CH_3)_3$), and the like, etc. Those salts derived from amines include salts with N-ethylpiperidine, procaine, dibenzylamine, N,N'-dibenzylethylenediamine, alkylamines or dialkylamines as well as salts with amino acids such as, for example, salts with arginine or lysine.

The term "amino protecting group" refers to protecting groups conventionally used to replace an acidic proton of an amino group. Examples of such groups are described in Green, T., Protective Groups in Organic Synthesis, Chapter 7, John Wiley and Sons, Inc. (1981), pp. 218–287. These examples include e.g. allyl, allyloxycarbonyl, t-butyl, t-butoxycarbonyl, benzyl, p-methoxybenzyl and p-nitrobenzyl. Preferred is allyloxycarbonyl.

The term "carboxylic acid protecting group" refers to protecting groups conventionally used to replace the acidic proton of a carboxylic acid. Examples of such groups are described in Greene, T., Protective Groups in Organic Synthesis, Chapter 5, pp. 152–192 (John Wiley and Sons, Inc. 1981). These examples include e.g. allyl, diphenylmethyl, p-nitrobenzyl, p-methoxybenzyl, trimethylsilyl, triethylsilyl, t-butyldimethylsilyl. Preferred is allyl.

As readily hydrolyzable esters of the compounds of formula I there are to be understood compounds of formula I, the carboxy group(s) of which (for example, the 2-carboxy group) is/are present in the form of readily hydrolyzable ester groups. Examples of such esters, which can be of the conventional type, are the lower alkanoyloxy-alkyl esters (e.g., the acetoxymethyl, pivaloyloxymethyl, 1-acetoxyethyl and 1-pivaloyloxyethyl ester), the lower alkoxycarbonyloxyalkyl esters (e.g., the methoxycarbonyloxymethyl, 1-ethoxycarbonyloxyethyl and 1-isopropoxycarbonyloxyethyl ester), the lactonyl esters (e.g., the phthalidyl and thiophthalidyl ester), the lower alkoxymethyl esters (e.g., the methoxymethyl ester) and the lower alkanoylaminomethyl esters (e.g., the acetamidomethyl ester). Other esters (e.g., the benzyl and cyanomethyl esters) can also be used. Other examples of such esters are the following: (2,2-dimethyl-1-oxopropoxy) methyl ester, 2-[(2-methylpropoxy)carbonyl]-2-pentenyl ester, 1-[[(1-methylethoxy)carbonyl]oxy] ethyl ester, 1-(acetyloxy) ethyl ester, (5-methyl-2-oxo-1,3-dioxol-4-yl) methyl ester, 1-[[(cyclohexyloxy)carbonyl]oxy] ethyl ester and 3,3-dimethyl-2-oxobutyl ester. It will be appreciated by those of ordinary skill in the art that the readily hydrolyzable esters of the compounds of the present invention can be formed at a free carboxy group of the compound, for example, at the carboxy group in position 2 of the isooxacephem ring.

Examples of salts of the compounds of formula I are defined under "pharmaceutically acceptable salts" above.

The compounds of formula I as well as their salts and readily hydrolyzable esters can be hydrated. The hydration can be effected in the course of making the compounds or can occur gradually as a result of hygroscopic properties of an initially anhydrous product.

The compounds of the present invention are useful for the treatment and prophylaxis of infectious diseases in mammals, both human and non-human. They also possess good oral absorption properties.

The products in accordance with the invention can be used as medicaments, for example, in the form of pharmaceutical preparations for enteral (oral) administration. The products in accordance with the invention can be administered, for example, perorally, such as in the form of tablets, coated tablets, dragees, hard and soft gelatine capsules, solutions, emulsions or suspensions, or rectally, such as in the form of suppositories.

Pharmaceutical compositions containing these compounds can be prepared using conventional procedures familiar to those skilled in the art, such as by combining the ingredients into a dosage form together with suitable, non-toxic, inert, therapeutically compatible solid or liquid carrier materials and, if desired, the usual pharmaceutical adjuvants.

It is contemplated that the compounds are ultimately embodied into compositions of suitable oral or parenteral dosage forms. The compositions of this invention can contain, as optional ingredients, any of the various adjuvants which are used ordinarily in the production of pharmaceutical preparations. Thus, for example, in formulating the present compositions into the desired oral dosage forms, one may use, as optional ingredients, fillers, such as coprecipitated aluminum hydroxide-calcium carbonate, dicalcium phosphate or lactose; disintegrating agents, such as maize starch; and lubricating agents, such as talc, calcium stearate, and the like. It should be fully understood, however, that the optional ingredients herein named are given by way of example only and that the invention is not restricted to the use hereof. Other such adjuvants, which are well known in the art, can be employed in carrying out this invention.

Suitable as such carrier materials are not only inorganic, but also organic carrier materials. Thus, for tablets, coated tablets, dragees and hard gelatine capsules there can be used, for example, lactose, maize starch or derivatives thereof, talc, stearic acid or its salts. Suitable carriers for soft gelatine capsules are, for example, vegetable oils, waxes, fats and semi-solid and liquid polyols (depending on the nature of the active substance; no carriers are, however, required in the case of soft gelatine capsules). Suitable carrier materials for the preparation of solutions and syrups are, for example, water, polyols, saccharose, invert sugar and glucose. Suitable carrier materials for suppositories are, for example, natural or hardened oils, waxes, fats and semi-liquid or liquid polyols.

As pharmaceutical adjuvants there are contemplated the usual preservatives, solubilizers, stabilizers, wetting agents, emulsifiers, sweeteners, colorants, flavorants, salts for varying the osmotic pressure, buffers, coating agents and antioxidants.

The compounds of formula I and their salts, or hydrates, can preferably be used for parenteral administration, and for this purpose are preferably made into preparations as lyophilisates or dry powders for dilution with customary agents, such as water or isotonic common salt solution.

Depending on the nature of the pharmacologically active compound the pharmaceutical preparations can contain the compound for the prevention and treatment of infectious diseases in mammals, human and non-human, a daily dosage of about 10 mg to about 4000 mg, especially about 50 mg to about 3000 mg, is usual, with those of ordinary skill in the art appreciating that the dosage will depend also upon the age, conditions of the mammals, and the kind of diseases being prevented or treated. The daily dosage can be administered in a single dose or can be divided over several doses. An average single dose of about 50 mg, 100 mg, 250 mg, 500 mg, 1000 mg, and 2000 mg can be contemplated.

Representative compounds of the present invention were tested.

In vitro activity was determined by minimum inhibitory concentration in a microorganism spectrum by the agar dilution method in Mueller Hinton agar.

The following compounds were tested:

(E)-(6S,7S)-7-[(Z)-2-(2-Amino-thiazol-4-yl)-2-cyclopentyloxyimino-acetylamino]-8-oxo-3-[(E)-2-oxo-1-(2,2,2-trifluoro-ethyl)-pyrrolidin-3-ylidenmethyl]-4-oxa-1-aza-bicyclo [4.2.0.] oct-2-ene-2-carboxylic acid sodium salt (Example 24).

(E)-(6S,7S)-7-[(Z)-2-(2-Amino-thiazol-4-yl)-2-cyclopentyloxyimino-acetylamino]-8-oxo-3-[(E)-2-oxo-1-phenyl-pyrrolidin-3-ylidenmethyl]-4-oxa-1-aza-bicyclo[4.2.0.] oct-2-ene-2-carboxylic acid sodium salt (Example 25).

(E)-(6S,7S)-7-[(Z)-2-(2-Amino-thiazol-4-yl)-2-cyclopentyloxyimino-acetylamino]-8-oxo-3-[(E)-1-(4-nitro-benzyl)-2-oxo-pyrrolidin-3-ylidenemethyl]-4-oxa-1-aza-bicyclo[4.2.0.] oct-2-ene-2-carboxylic acid sodium salt (Example 26).

(E)-(6S,7S)-7-[(Z)-2-(2-Amino-thiazol-4-yl)-2-cyclopentyloxyimino-acetylamino]-8-oxo-3-[(E)-1-(cyclopropyl)-2-oxo-pyrrolidin-3-ylidenemethyl]-4-oxa-1-aza-bicyclo[4.2.0.] oct-2-ene-2-carboxylic acid sodium salt (Example 27).

(E)-(6S,7S)-7-[(Z)-2-(2-Amino-thiazol-4-yl)-2-cyclopentyloxyimino-acetylamino]-8-oxo-3-[(E)-1-(isobutyl)-2-oxo-pyrrolidin-3-ylidenemethyl]-4-oxa-1-aza-bicyclo[4.2.0.] oct-2-ene-2-carboxylic acid sodium salt (Example 28).

(E)-(6S,7S)-7-[(Z)-2-(2-Amino-thiazol-4-yl)-2-cyclopentyloxyimino-acetylamino]-8-oxo-3-[(E)-1-(5-methyl-isooxazolyl)-2-oxo-pyrrolidin-3-ylidenemethyl]-4-oxa-1-aza-bicyclo[4.2.0.] oct-2-ene-2-carboxylic acid sodium salt (Example 29).

(E)-(6S,7S)-7-[(Z)-2-(2-Amino-thiazol-4-yl)-2-cyclopentyloxyimino-acetylamino]-8-oxo-3-[(E)-1-(3-nitrophenyl)-2-oxo-pyrrolidin-3-ylidenemethyl]-4-oxa-1-aza-bicyclo[4.2.0.] oct-2-ene-2-carboxylic acid sodium salt (Example 30).

(E)-(6S,7S)-7-[(Z)-2-(2-Amino-thiazol-4-yl)-2-cyclopentyloxyimino-acetylamino]-8-oxo-3-[(E)-1-(4-hydroxyphenyl)-2-oxo-pyrrolidin-3-ylidenemethyl]-4-oxa-1-aza-bicyclo[4.2.0.] oct-2-ene-2-carboxylic acid sodium salt (Example 31).

(E)-(6S,7S)-7-[(Z)-2-(2-Amino-thiazol-4-yl)-2-cyclopentyloxyimino-acetylamino]-3-[(E)-1-(2-fluoro-phenyl)-2-oxo-pyrrolidin-3-ylidenemethyl]-8-oxo-4-oxa-1-aza-bicyclo[4.2.0.] oct-2-ene-2-carboxylic acid sodium salt (Example 32).

(E)-(6S,7S)-7-[(Z)-2-(2-Amino-thiazol-4-yl)-2-cyclopentyloxyimino-acetylamino]-3-[2-oxo-1-(2-pyridinyl)-pyrrolidin-3-ylidenemethyl]-8-oxo-4-oxa-1-aza-bicyclo[4.2.0.] oct-2-ene-2-carboxylic acid sodium salt (Example 33).

(E)-(6S,7S)-7-[(Z)-2-(2-Amino-thiazol-4-yl)-2-cyclopentyloxyimino-acetylamino]-3-[(E)-1-(1-methyl-pyridinium-2-yl)-2-oxo-pyrrolidin-3-ylidenemethyl]-8-oxo-4-oxa-1-aza-bicyclo[4.2.0.] oct-2-ene-2-carboxylic acid (Example 34).

(E)-(6S,7S)-7-[(Z)-2-(2-Amino-thiazol-4-yl)-2-cyclopentyloxyimino-acetylamino]-3-[1-(2-methoxy-phenyl)-2-oxo-pyrrolidin-3-ylidenemethyl]-8-oxo-4-oxa-1-aza-bicyclo[4.2.0.] oct-2-ene-2-carboxylic acid sodium salt (Example 35).

(E)-(6S,7S)-7-[(Z)-2-(2-Amino-thiazol-4-yl)-2-carbamoylmethoxyimino-acetylamino]-3-[(E)-1-(4-nitro-benzyl)-2-oxo-pyrrolidin-3-ylidenemethyl]-8-oxo-4-oxa-1-aza-bicyclo[4.2.0.] oct-2-ene-2-carboxylic acid sodium salt (Example 36).

(E)-(6S,7S)-7-[(Z)-2-(2-Amino-thiazol-4-yl)-2-carbamoylmethoxyimino-acetylamino]-3-[(E)-1-(phenyl)-2-oxo-pyrrolidin-3-ylidenemethyl]-8-oxo-4-oxa-1-aza-bicyclo[4.2.0.] oct-2-ene-2-carboxylic acid sodium salt (Example 37).

(E)-(6S,7S)-7-[(Z)-2-(2-Amino-thiazol-4-yl)-2-carbamoylmethoxyimino-acetylamino]-3-[(E)-1-cyclopropyl-2-oxo-pyrrolidin-3-ylidenemethyl]-8-oxo-4-oxa-1-aza-bicyclo[4.2.0.] oct-2-ene-2-carboxylic acid sodium salt (Example 38).

(E)-(6S,7S)-7-[(Z)-2-(2-Amino-thiazol-4-yl)-2-carbamoylmethoxyimino-acetylamino]-3-[(E)-1-(5-methyl-isooxazolyl)-2-oxo-pyrrolidin-3-ylidenemethyl]-8-oxo-4-oxa-1-aza-bicyclo[4.2.0.] oct-2-ene-2-carboxylic acid sodium salt (Example 39).

(E)-(6S,7S)-7-[(Z)-2-(2-Amino-thiazol-4-yl)-2-carbamoylmethoxyimino-acetylamino]-3-[(E)-1-isobutyl-2-oxo-pyrrolidin-3-ylidenemethyl]-8-oxo-4-oxa-1-aza-bicyclo[4.2.0.] oct-2-ene-2-carboxylic acid sodium salt (Example 40).

(E)-(6S,7S)-7-[(Z)-2-(2-Amino-thiazol-4-yl)-2-carbamoylmethoxyimino-acetylamino]-3-[(E)-1-(3-nitrophenyl)-2-oxo-pyrrolidin-3-ylidenemethyl]-8-oxo-4-oxa-1-aza-bicyclo[4.2.0.] oct-2-ene-2-carboxylic acid sodium salt (Example 41).

(E)-(6S,7S)-7-[(Z)-2-(2-Amino-thiazol-4-yl)-2-hydroxyimino-acetylamino]-8-oxo-3-[(E)-1-(2-methoxy-phenyl)-2-oxo-pyrrolidin-3-ylidenemethyl]-4-oxa-1-aza-bicyclo[4.2.0.] oct-2-ene-2-carboxylic acid sodium salt (Example 42).

(E)-(6S,7S)-7-[(Z)-2-(2-Amino-thiazol-4-yl)-2-hydroxyimino-acetylamino]-8-oxo-3-[(E)-1-(isobutyl)-2-oxo-pyrrolidin-3-ylidenemethyl]-4-oxa-1-aza-bicyclo[4.2.0.] oct-2-ene-2-carboxylic acid sodium salt (Example 43).

(E)-(6S,7S)-7-[(Z)-2-(2-Amino-thiazol-4-yl)-2-hydroxyimino-acetylamino]-8-oxo-3-[(E)-1-(2-fluoro-phenyl)-2-oxo-pyrrolidin-3-ylidenemethyl]-4-oxa-1-aza-bicyclo[4.2.0.] oct-2-ene-2-carboxylic acid sodium salt (Example 44).

(E)-(6S,7S)-7-[(Z)-2-(2-Amino-thiazol-4-yl)-2-hydroxyimino-acetylamino]-8-oxo-3-[(E)-1-(3-nitro-phenyl)-2-oxo-pyrrolidin-3-ylidenemethyl]-4-oxa-1-aza-bicyclo[4.2.0.] oct-2-ene-2-carboxylic acid sodium salt (Example 45).

(E)-(6S,7S)-7-[(Z)-2-(2-Amino-thiazol-4-yl)-2-hydroxyimino-acetylamino]-8-oxo-3-[(E)-1-(pyridin-2-yl)-2-oxo-pyrrolidin-3-ylidenemethyl]-4-oxa-1-aza-bicyclo[4.2.0.] oct-2-ene-2-carboxylic acid sodium salt (Example 46).

(E)-(6S,7S)-7-[(Z)-2-(2-Amino-thiazol-4-yl)-2-hydroxyimino-acetylamino]-8-oxo-3-[(E)-1-(4-nitro-benzyl)-2-oxo-pyrrolidin-3-ylidenemethyl]-4-oxa-1-aza-bicyclo[4.2.0.] oct-2-ene-2-carboxylic acid sodium salt (Example 47).

(E)-(6S,7S)-7-[(Z)-2-(2-Amino-thiazol-4-yl)-2-hydroxyimino-acetylamino]-8-oxo-3-[(E)-1-(5-methyl-isooxazolyl)-2-oxo-pyrrolidin-3-ylidenemethyl]-4-oxa-1-aza-bicyclo[4.2.0.] oct-2-ene-2-carboxylic acid sodium salt (Example 48).

(E)-(6S,7S)-7-[[3-(2,6-Dichloro-phenyl)-5-methyl-isoxazol-4-yl-carbonyl]-amino]-3-[(E)-1-(isobutyl)-2- oxo-pyrrolidin-3-ylidenemethyl]-4-oxa-1-aza-bicyclo [4.2.0.] oct-2-ene-2-carboxylic acid sodium salt (Example 49).

(6S,7S)-3-((E)-1-Isobutyl-2-oxo-pyrrolidin-3-ylidenemethyl)-7[2-(1-methyl-1H-tetrazol-5-ylsulfanyl)-acetylamino)-8-oxo-4-oxa-1-aza-bicyclo [4.2.0.] oct-2-ene-2-carboxylic acid sodium salt (Example 50).

(6S,7S)-7-Acetylamino-3-((E)-1-isobutyl-2-oxo-pyrrolidin-3-ylidenemethyl)-8-oxo-4-oxa-1-aza-bicyclo[4.2.0.] oct-2-ene-2-carboxylic acid sodium salt (Example 51).

The results appear below:

| | Minimum Inhibiting Concentration Values (mg/l) | | | | | |
|---|---|---|---|---|---|---|
| Example No. | S. aureus 6538 | S. aureus 887 | E. faecalis ATCC 29212 | E. faecium QK 5/90 | E. coli 25922 | E. cloacae 908SSi |
| 24 | 4 | 4 | 4 | 4 | 8 | 8 |
| 25 | 4 | 4 | 1 | 8 | 4 | 8 |
| 26 | 4 | 4 | 2 | 4 | 8 | 8 |
| 27 | 4 | 4 | 2 | 4 | 4 | 8 |
| 28 | 2 | 4 | 1 | 4 | 4 | 8 |
| 29 | 4 | 8 | 1 | 8 | 8 | 8 |
| 30 | 2 | 2 | 1 | 4 | 2 | 8 |
| 31 | 2 | 2 | 1 | 4 | 4 | 8 |
| 32 | 8 | 4 | 2 | 8 | 8 | 8 |
| 33 | 16 | 8 | 2 | 8 | 8 | 16 |
| 34 | 16 | 16 | 16 | >32 | >32 | >32 |
| 35 | 4 | 2 | 2 | 8 | 2 | 4 |
| 36 | 4 | 4 | 32 | 32 | 1 | >32 |
| 37 | 4 | 4 | 32 | 32 | 1 | 1 |
| 38 | 8 | 8 | 32 | >32 | 0.12 | 0.5 |
| 39 | 4 | 4 | 16 | 32 | 0.5 | 1 |
| 40 | 8 | 8 | 32 | >32 | 0.5 | 1 |
| 41 | 4 | 4 | 16 | 32 | 1 | 2 |
| 42 | 1 | 2 | 0.5 | 16 | 2 | 8 |
| 43 | 1 | 1 | 1 | 32 | 1 | 2 |
| 44 | 1 | 1 | 0.5 | 16 | 1 | 4 |
| 45 | 1 | 1 | 1 | 16 | 2 | 2 |
| 46 | 0.5 | 1 | 0.5 | 16 | 1 | 2 |
| 47 | 1 | 0.5 | 2 | 16 | 2 | 2 |
| 48 | 1 | 1 | 1 | 32 | 1 | 2 |
| 49 | — | 1 | — | — | >32 | — |
| 50 | — | 2 | — | — | 8 | — |
| 51 | — | 4 | — | — | 16 | — |

The compounds of the formula I in accordance with the invention as well as their pharmaceutical acceptable salts, hydrates, or readily hydrolyzable esters can be made in accordance with the invention by (a) treating a compound having the formula III

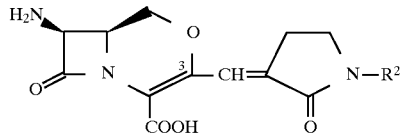

in which $R^2$ is as defined above under formula I or an ester or salt thereof, with acylating agents, or (b) for making of a compound of formula I in which $R^1$ and/or $R^2$ may contain free amino, hydroxy or carboxylic group(s) cleaving off the amino, hydroxy and/or carboxy protecting group(s) or reducing a nitro group to amino in a compound having the formula IV

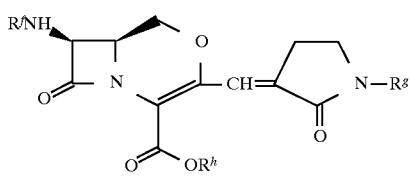

in which $R^h$ is hydrogen or a carboxy protecting group, $R^f$ is as $R^1$ and $R^g$ is as $R^2$ with the proviso that at least one of the following provisions is fulfilled:

(i) $R^h$ is a carboxylic acid protecting group, (ii) $R^f$ is a residue defined under $R^1$ having nitro, protected amino, protected hydroxy and/or protected carboxylic group(s), (iii) $R^g$ is a residue defined under $R^2$ having nitro, protected amino, protected hydroxy and/or protected carboxylic group(s), or a salt thereof, or (c) for making of a readily hydrolyzable ester of a compound of formula I subjecting a carboxylic acid of formula I to a corresponding esterification, or (d) for making of salts or hydrates of a compound of formula I or hydrates of said salts converting a compound of formula I into a salt or hydrate or into a hydrate of said salts.

The reaction of compounds III with acylating agents according to embodiment (a) can be carried out in a manner known per se.

Examples of acylating agents used in embodiment (a) are activated carboxylic acids such as acid chlorides, anhydrides, reactive esters such as N-hydroxysuccinimide esters, 2-benzothiazolyl thioesters, or 1-hydroxybenzotriazole esters of the carboxylic acids. For instance, the 2-benzothiazolyl thioester may be reacted with the compound of the formula III in an inert organic solvent such as in dimethylformamide, methylene chloride, ethyl acetate and the like. The 1-hydroxybenzotriazole ester can be employed by reacting the carboxylic acid with 1-hydroxybenzotriazole and a carbodiimide, especially N,N'-dicyclohexylcarbodiimide or N,N'-diisopropylcarbodiimide in an inert organic solvent, preferably methylene chloride, dimethylformamide, tetrahydrofuran, acetonitrile or ethyl acetate.

The carboxy group in compounds of the formula III can be protected; for example, by esterification to form a readily cleavable ester such as allyl-, t-butyl-, benzhydryl-, p-nitrobenzyl, p-methoxybenzyl-ester.

The 7-amino group in compounds of the formula III can be protected, for example, by those groups employed in peptide chemistry, such as allyloxycarbonyl, t-butoxycarbonyl, p-nitrobenzyloxycarbonyl or benzyloxycarbonyl, trityl or benzhydryl. Preferred is allyloxycarbonyl.

The reaction of a 7-amino compound of formula III with a carboxylic acid or a reactive derivative thereof can conveniently be carried out at a temperature between about −40° C. and +60° C., e.g. at room temperature.

Compound of the formula III can be obtained by palladium assisted deprotection of the corresponding allylester IVa

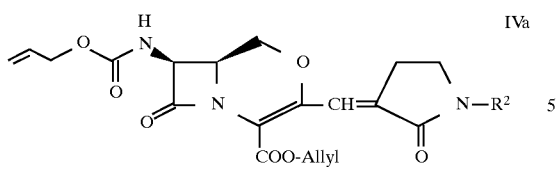

wherein R² is as defined above.

or in case of esters other than allylesters being used by cleaving off the allyloxycarbonyl-amino-protecting group, adding the acylating agent and cleaving off the ester-group.

Embodiment (b) of the process of the present invention involves deprotection (removal) of protected amino, hydroxy or carboxylic groups present in a compound of formula IV and can be carried and as follows:

Removal of amino protecting groups

The amino protecting groups may be cleaved off by acid hydrolysis (e.g. the t-butoxycarbonyl group or trityl group), using e.g. aqueous formic acid.

In the case of an allyloxycarbonyl protecting group Pd(0) (- produced in situ by reduction of Pd-bis triphenylphosphin-dichloride with a trialkyltinhydride -) is employed at a temperature in the range of about −30° C. to +40° C. in the presence of a Pd-π-complex scavenger like dimedon, pyrrolidin, dialkylmalonat, trialkyltinhydride, in an aprotic solvent such as dichlormethane, hexane, diethylether, toluol or tetrahydrofuran.

Removal of hydroxy protecting groups

Possible hydroxy protecting groups are such as are commonly known in the art, e.g. benzyl or p-nitrobenzyl.

For protection of hydroxyimino groups trityl or acetyl can be employed.

These protecting groups are e.g. removed as follows:
- trityl in acidic solvents like 90% formic acid at about 0° C. to 50° C. or triethylsilane in trifluoroacetic acid at about −20° C. to 25° C.; in organic solutions of hydrochloric acid at about −50° C. to 25° C.;
- acetyl with weak inorganic bases like sodium bicarbonate in ethanol/water at about 0° C. to 50° C.;
- benzyl, p-nitrobenzyl with hydrogen or a hydrogen donor like cyclohexene or cyclohexadiene and a catalyst like Pd/C in solvents like alcohols, dichloromethane, ethyl acetate, acetic acid, dimethylformamide etc, or mixtures of these at about 0° C. to 50° C.

Removal of protecting groups at the carboxy function

As ester protecting groups one may utilize an ester form which can be easily converted into a free carboxyl group under mild conditions, the ester protecting group being exemplified by, for example, t-butyl, p-nitrobenzyl, p-methoxybenzyl, benzhydryl, allyl, etc.

These protecting groups may be removed as follows:
benzhydryl trifluoroacetic acid with anisol, phenol, cresol or triethylsilane at about −40° C. to room temperature; hydrogen with Pd/C in an alcohol such as ethanol or in tetrahydrofuran;

BF₃-etherate in acetic acid at about 0° C. to 50° C.;
t-butyl formic acid or trifluoroacetic acid with or without anisol, phenol, cresol or triethylsilane and a solvent such as dichloromethane at about −10° C. to room temperature;
p-nitrobenzyl sodium sulfide in acetone/water at about 0° C. to room temperature; or hydrogen with Pd/C in an alcohol such as ethanol or in tetrahydrofuran;
p-methoxybenzyl formic acid at about 0° C. to 50° C.; or trifluoroacetic acid and anisol, phenol or triethylsilane at about −40° C. to room temperature;
allyl palladium(0) catalyzed transalkylation reaction in the presence of sodium or potassium salt of 2-ethyl hexanoic acid, see for example J. Org. Chem. 1982, 47, 587.

In order to make a readily hydrolyzable ester of the carboxylic acids of formula I in accordance with embodiment (c) of the process provided by the present invention, a carboxylic acid of formula I is preferably reacted with a corresponding halide, preferably an iodide, containing the desired ester group. The reaction can be accelerated with the aid of a base such as an alkali metal hydroxide, an alkali metal carbonate or an organic amine such as triethylamine. The esterification is preferably carried out in an inert organic solvent such as dimethylacetamide, hexamethylphosphoric acid triamide, dimethyl sulfoxide or, especially, dimethylformamide. The reaction is preferably carried out at a temperature in the range of about 0° C. to 40° C.

The making of the salts and hydrates of the compounds of formula I or the hydrates of said salts in accordance with embodiment (d) of the process provided by the present invention can be carried out in a manner known per se; for example, by reacting a carboxylic acid of formula I or a salt thereof with an equivalent amount of the desired base, conveniently in a solvent such as water or an organic solvent (e.g. ethanol, methanol, acetone and the like). Correspondingly, salt formation is brought about by the addition of an organic or inorganic salt. The temperature at which the salt formation is carried out is not critical. The salt formation is generally carried out at room temperature, but it can be carried out at a temperature slightly above or below room temperature, for example in the range of 0° C. to +50° C.

The making of the hydrates usually takes place automatically in the course of the manufacturing process or as a result of the hygroscopic properties of an initially anhydrous product. For the controlled manufacture of a hydrate, a completely or partially anhydrous carboxylic acid of formula I or salt thereof can be exposed to a moist atmosphere (e.g. at about +10° C. to +40° C.).

Exemplary of the process for obtaining products in accordance with the invention are the following reaction scheme 1 below. Scheme 1 shows the process for obtaining compounds in accordance with the invention, e.g. a compound of formula II.

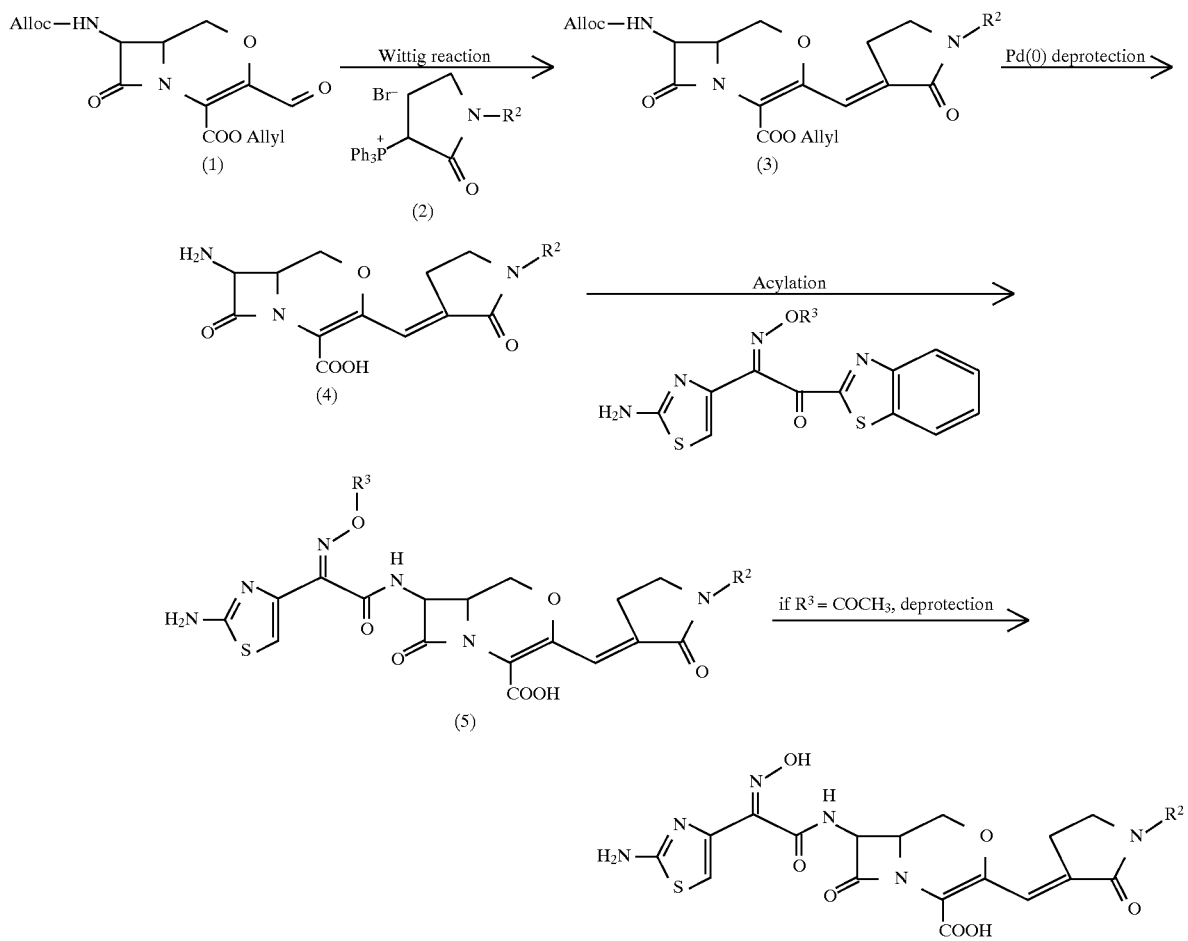

Scheme 1

Scheme 1

Wittig reaction 1 to 3

The reaction of known 3-isooxacephem aldehyde (1) wherein the 7-amino-protecting group is allyloxycarbonyl and the carboxy protecting group is allyl with a Wittig reagent (2) yields the coupling product (3). The reaction is carried out in the presence of a base which is either an inorganic base (sodium or potassium hydroxide, sodium or potassium carbonate etc.), an organic base (tertiary amines), an organolithium compound such as butyl lithium or phenyl lithium or an epoxide such as 1,2-butyleneoxide. The preferred solvents are in the case of inorganic base being used, water and water-miscible solvents (acetone, tetrahydrofuran, or alcohols etc.); in the case of organic base being used, an inert solvent such as methylene chloride, chloroform, benzene, tetrahydrofuran; in the case of organolithium being used, benzene or tetrahydrofuran; and in the case an epoxide being used, the epoxide itself (e.g. 1,2-butyleneoxide). The temperature for the reaction ranges from −20° C. to 80° C. The preferred conditions are exemplified in the examples.

In the normal Wittig Reaction according to scheme 1, the E isomer is the predominant product. Invariably, less than 10% Z-isomer is formed, the amount depending on the reagents and conditions.

The making of the Wittig reagent (2) can be carried out in a manner known per se; for example, by cyclization of a N-substituted dibromide using a catalyst like Dowex as described in the European Patent Application EPA 0 620 255.

Deprotection 3 to 4

The carboxylic acid protecting group $R^h$ and the amino protecting group $R^f$ are removed and the reaction conditions used are depending on the nature of the protecting groups.

In the case of the amino protecting group being allyloxycarbonyl and the carboxy protecting group being the allyl ester, Pd(0) generated in situ is employed. In the case of the amino protecting group being t-butoxycarbonyl and the carboxy protecting group being benzhydryl, trifluoroacetic acid is employed, at temperature of about −20° C. to about room temperature.

Acylation 3 to 4

The acylation of compound (4) can be carried out with an organic acid which is activated with known reagents, preferably anhydride, thionyl chloride, oxalyl chloride, dicyclohexylcarbodiimide, bis-[benzthiazolyl-(2)]disulfide, N-hydroxy benzotriazole or a 2-halo N-methylpyridinium salt. The reaction is carried out with or without the base (inorganic or organic bases) depending on the method of activation and a wide range of solvents, from water and water-miscible solvent to inert solvents such as chloroform, dimethylformamide (DMF) or dimethylsulfoxide (DMSO) can be used. The $R^3$ group, if necessary, can be further deprotected with a reaction condition suitable for the removal of the protecting group.

The 2-carboxylic function of compound (5) is converted to the prodrug esters which are readily hydrolyzable in vivo.

Scheme 2 shows the making of the isooxacephemaldehydes (1) of Scheme 1.

15

Scheme 2

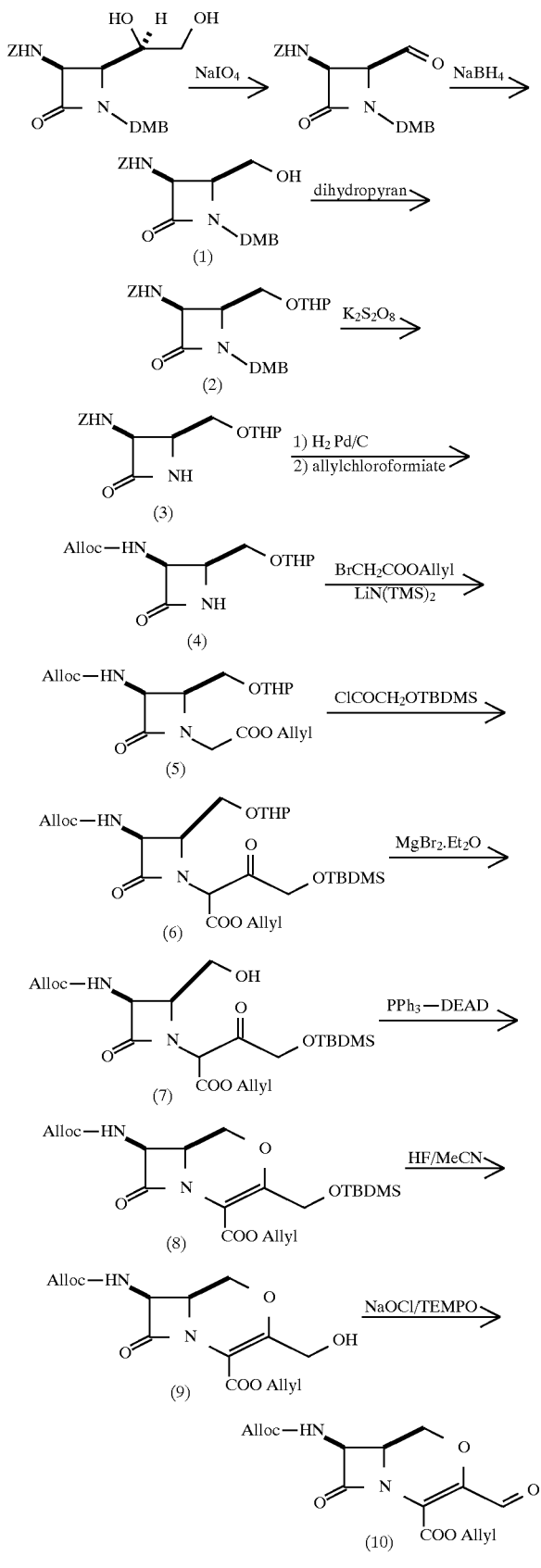

16

-continued
Scheme 2

Z = benzyloxycarbonyl,; THP = tetrahydropyranyl; DMB = 2,4-dimethoxybenzyl; Alloc = allyloxycarbonyl; TBDMS = tert-butyldimethylsilyl; DEAD = diethylazodicarboxylate The making of starting materials according to Scheme 2 are illustrated in the following description termed "Preparations 1–9".

Examples 1–23 show the preparation of diallyl vinyl isooxacephems according to the Wittig reaction Scheme 1, 1 to 3.

Subsequent thereto follow "Examples 24–51" which illustrate the making of the end products of the present invention.

I Preparation of the key-aldehydes

Preparation 1 (1 to 2, Scheme 2)

1:1 Mixture of (3S,4S)-[1-(2,4-Dimethoxy-benzyl)-2-oxo-4[(R)-and -[(S)-tetrahydropyran-2-yloxymethyl]-azetidin-3-yl]-carbamic acid benzyl ester 1 g (5.25 mmol) p-toluenesulfonic acid mono-hydrate was added to a suspension of 107 g (0.267 mol) benzyl-(2S,3S)-1-(2,4-dimethoxybenzyl)-2-(hydroxymethyl)-4-oxo-3-azetidinyl-carbamate in 1 l tetrahydrofuran. 41.6 ml (38,6 g; 0,458 mol) 3,4-dihydro-2H-pyran were added dropwise within two hours at room temperature. The reaction mixture was stirred for six days. The reaction was controlled via thin layer chromatography (eluent: ethyl acetate/n-hexane 1:1, Rf educt: 0.09, Rf product: 0.18). The solvent was removed on a rotary evaporator. The residue was purified by chromatography over silica gel using ethyl acetate/n-hexane 1:1 as eluent. The obtained oil was stirred in n-hexane. The obtained crystals were filtered off and dried at high vacuum.

Yield: 110 g (85%) white crystals.

IR (cm$^{-1}$): 3294, 1758, 1686, 1546, 1293, 1267

MS (ISP): 485.3 (M+H)$^+$; 507.2 (M+Na)$^+$

Preparation 2 (2 to 3, Scheme 2)

1:1 Mixture of (3S,4S) [-2-Oxo-4-[(R)-and-[(S)-tetrahydropyran-2-yloxymethyl]-azetidin-3-yl]-carbamic acid benzyl ester 110 g (0.227 mol) of a 1:1 mixture of (3S,4S)-[1-(2,4-dimethoxy-benzyl)-2-oxo-4[(R)-and -[(S)-tetrahydropyran-2-yloxymethyl]-azetidin-3-yl]-carbamic acid benzyl ester were dissolved in 1 l acetonitrile and diluted with 0.5 l water. The reaction mixture was heated to 80° C. Then 128 g (0.467 mol) potassium persulfate were added in two portions within two hours. The reaction mixture was adjusted to pH 5.5 by adding 2N sodium carbonate solution. After 3 hours the reaction mixture was cooled to room temperature, diluted with 1.5 l ethyl acetate and saturated with sodium chloride. The reaction mixture was adjusted to pH 7 by adding 2N sodium carbonate solution. The organic phase was separated, dried over magnesium sulfate, filtered off and concentrated on a rotary evaporator. The residue was purified by chromatography over silica gel using ethyl acetate/n-hexane 7:3 as eluent.

Yield: 60 g (79%) yellow oil.

IR (cm$^{-1}$): 3294, 1764, 1718, 1536, 1252

MS (ISP): 335.2 (M+H)$^+$; 352.2 (M+NH$_4$)$^+$; 357.2 (M+Na)$^+$

Preparation 3 (3 to 4, Scheme 2)

1:1 mixture of (3S,4S) [-2-Oxo-4[(R)-and-[(S)-tetrahydropyran-2-yloxymethyl]-azetidin-3-yl]-carbamic acid allyl ester 60 g (0.179 mol) of a 1:1 mixture of (3S,4S) [-2-oxo-4-[(R)-and-[(S)-tetrahydropyran-2-yloxymethyl]-azetidin-3-yl]-carbamic acid benzyl ester were dissolved in 800 ml ethyl acetate and hydrogenated over 5 g palladium-charcoal (10% Pd). The suspension was stirred under hydrogen at normal pressure. The catalyst was filtered off over glass fiber under suction and the filtrate was concentrated on a rotary evaporator. The obtained colorless oil was dried at high vacuum, dissolved in 700 ml methylene chloride and cooled to −20° C. The reaction mixture was stirred vigorously and 15.9 ml (15.6 g, 0.197 mol) pyridine were added. A solution of 21 ml (23.81 g, 0.197 mol ) allylchloroformate in 100 ml methylene chloride was added dropwise within 30 minutes raising the temperature to −10° C. The reaction mixture was stirred at −10° C. for a further 2 hours, diluted with 500 ml methylene chloride and extracted in succession with water (500 ml), 0.1M HCl (500 ml) and 20% sodium chloride solution (500 ml). The organic phase was dried over magnesium sulfate, filtered off and concentrated on a rotary evaporator. The residue was purified by chromatography over silica gel using ethyl acetate/n-hexane 1:1 as eluent.

Yield: 44.8 g (88%) colorless oil.

IR (cm$^{-1}$): 3293, 1764, 1724, 1537, 1259

MS (ISP): 285,3 (M+H)$^+$; 302,3 (M+NH$_4$)$^+$; 307,2 (M+Na)$^+$

Preparation 4 (4 to 5, Scheme 2)

1:1 mixture of (3S,4S)-[3-allyloxycarbonylamino-2-oxo-4[(R)-and[(S)-tetrahydro-pyran-2-yloxymethyl]-azetidin-1-yl]-acetic acid allyl ester 12.3 g (0.089 mol) potassium carbonate were added to a solution of a 1:1 mixture of (3S,4S) [-2-oxo-4-[(R)-and-[(S)-tetrahydropyran-2-yloxymethyl]-azetidin-3-yl]-carbamic acid allyl ester (19.5 g; 0.068 mol) in 200 ml dimethylformamide. Then 13.5 g (0.075 mol) bromoacetic acid allyl ester were added dropwise at room temperature. The reaction mixture was stirred for 48 hours and filtered off over glass fiber under suction. The filtrate was concentrated on a rotary evaporator. The residue was taken up in 500 ml ethyl acetate and extracted with 20% sodium chloride solution. The organic phase was dried over magnesium sulfate and concentrated on a rotary evaporator. The residue was purified by chromatography over silica gel using ethyl acetate/n-hexane 1:1 as eluent.

Yield: 16 g (61%) colorless oil.

IR (cm$^{-1}$): 3312, 1770, 1726, 1535, 1420, 1248

MS (ISP): 383.2 (M+H)$^+$; 405.2 (M+Na)$^+$

Preparation 5 (5 to 6, Scheme 2)

1:1 mixture of 2-[(3S,4S)-3-Allyloxycarbonylamino-2-oxo-4[(R)-and-[(S)-tetrahydro-pyran-2-yloxynethyl]-azetidin-1-yl]-4(tert-butyl-silylanyloxy)-3-oxo-butyric acid allyl ester 24 g (0.063 mol) of a 1:1 mixture of (3S,4S)-[3-allyloxycarbonylamino-2-oxo-4-[(R)-and[(S)-tetrahydro-pyran-2-yloxymethyl]-azetidin-1-yl]-acetic acid allyl ester were dissolved in 300 ml tetrahydrofuran and cooled to −78° C. A solution of 1M bis-trimethylsilyl-litium-amide in tetrahydrofuran (63 ml, 0.063 mol) was added dropwise at −78° C. After 30 minutes 8.03 ml (0.063 mol) trimethylchlorsilan were added dropwise and the reaction mixture was stirred for a further 45 min. Then a further solution of 1M bis-trimethylsilyl litium-amide in tetrahydrofuran (126 ml, 0.126 mol) was added dropwise. After 30 minutes 14.4 g (0.0689 mol) tert.-butyl-dimethylsilyloxy-acetylchloride were added. The reaction mixture was stirred for a further 2 hours at −78° C. The temperature was raised to −20° C., kept at −20° C. for one hour, cooled again to −78° C. and treated with a saturated solution of ammonium chloride (200 ml). The temperature was raised to 0° C. The reaction mixture was adjusted to pH 5 by adding 2N HCl. Then 300 ml ethyl acetate were added. The organic phase was washed with water (300 ml ) and aqueous sodium chloride solution (300 ml). The organic solution was dried over magnesium sulphate and concentrated on a rotary evaporator. The residue was chromatographed over silica gel using ethyl acetate/n-hexane 3:7 as eluent.

Yield: 24 g (70%) colorless oil.

IR (cm$^{-1}$): 3316, 2949, 1775, 1734, 1650, 1527, 1251

MS (ISP): 555.3 (M+H)+; 572.4 (M+NH4)+

Preparation 6 (6 to 7, Scheme 2)

2-[(3S,4S)-3-Allyloxycarbonylamino2-hydroxymethyl-4-oxo-azetidin-1-yl]-4-(tert-butyl-silylanyloxy)-3-oxo-butyric acid allyl ester 15.5 g (0.060 mol) magnesium bromide-diethyletherate were added portionwise at 0° C. to a solution of a 1:1 mixture of 2-[(3S,4S)-3-Allyloxycarbonylamino-2-oxo-4[(R)-and -[(S)-tetrahydro-pyran-2-yloxymethyl]-azetidin-1-yl]-4-(tert-butyl-silylanyloxy)-3-oxo-butyric acid allyl ester (11.6 g, 0.020 mol) in 300 ml diethylether. After 2 hours 150 ml water were added at 0° C. The organic phase was washed with a saturated solution of sodium chloride and dried over magnesium sulfate. The solvent was evaporated and the residue was chromatographed over silica gel using ethyl acetate/n-hexane 1:1 as eluent.

Yield: 5.9 g (62%) yellow oil.

IR (cm−1): 3403, 1735, 1648, 1520, 1254

MS (EI): 470 (M); 413 (M-tBu)

Preparation 7 (7 to 8, Scheme 2)

(6S,7S)-7-Allyloxycarbonylamino3-(tert-butyl-dimethyl-silanyloxymethyl)-8-oxo-4-oxa-1-aza-bicyclo[4.2.0.] oct-2-ene-2-carboxylic acid allyl ester To a solution of 2-[(3S,4S)-3-Allyloxycarbonylamino-2-hydroxymethyl-4-oxo-azetidin-1-yl]-4-(tert-butyl-silylanyloxy)-3-oxo-butyric acid allyl ester (5.9 g, 0.0125 mol) in 100 ml tetrahydrofuran 4.9 g (18.8 mmol) triphenylphosphin were added at −30° C. After 5 minutes 2.7 ml (17.5 mmol) azodicarboxylic acid diethyl ester were added dropwise. The temperature was raised to 0° C. and the reaction mixture was stirred for 30 minutes at 0° C. Then 20 ml saturated ammonium chloride solution were added. The reaction mixture was diluted with 150 ml ethyl acetate. The organic phase was dried over magnesium sulfate. The solvent was evaporated and the residue was chromatographed over silica gel using ethyl acetate/n-hexane 3:7 as eluent.

Yield: 3.4 g (60%) yellow oil.

IR (cm−1): 3320, 1785, 1717, 1616, 1540, 1467

MS (ISP): 453.3 (M+H)+; 470.3 (M+NH4)+

Preparation 8 (8 to 9, Scheme 2)

6S,7S)-7-Allyloxycarbonylamino-3hydroxymethyl-8-oxo-4-oxa-1-aza-bicyclo[4.2.0.] oct-2-ene-2carboxylic acid allyl ester 3.4 g (7.5 mmol) (6S,7S)-7-Allyloxycarbonylamino-3-(tert-butyl-dimethyl-silanyloxymethyl)-8-oxo-4-oxa-1-azabicyclo [4.2.0.] oct-2-ene-2-carboxylic acid allyl ester were dissolved in 20 ml acetonitrile. The solution was cooled to 0° C. 7.5 ml (0.015 mol) 2N HF in acetonitrile were added. The reaction mixture was warmed to room temperature and was stirred for 3 hours. The obtained solution was cooled to 0° C. and diluted with 100 ml ethyl acetate. The solution was adjusted to pH 6.5 by adding saturated sodium bicarbonate solution. The organic phase was washed with saturated sodium chloride solution and dried over magnesium sulfate. The solvent was evaporated and the residue was chromatographed over silica gel using ethyl acetate/n-hexane 1:1 as eluent.

Yield: 2.3 g (88%) oil.

IR (cm−1): 3474, 3330, 1777, 1710, 1611, 1540

MS (ISP): 321.2 (M+H−H2O); 339.2 (M+H)+; 361.1 (M+Na)+

Preparation 9 (9 to 10, Scheme 2)

(6S,7S)-7-Allyloxycarbonylamino-3-formyl-8-oxo-4-oxa-1-aza-bicyclo[4.2.0.] oct-2-ene-2-carboxylic acid allyl ester 845 mg (2.5 mmol) (6S,7S)-7-Allyloxycarbonylamino-3-hydroxymethyl-8-oxo-4-oxa-1-aza-bicyclo[4.2.0.] oct-2-ene-2-carboxylic acid allyl ester were dissolved in 20 ml methylene chloride. At 0° C. 47 mg (0.39 mmol) potassium bromide, 106 mg (1.26 mmol) sodium bicarbonate and 5 ml water were added. Then 59.7 mg (0.38 mmol) 2,2,6,6-tetramethylpiperidine-1-oxyl were added. The reaction mixture was stirred vigorously and 2.5 ml 12% sodium hypochlorite solution were added dropwise. After 30 minutes at 0° C. the reaction mixture was diluted with 100 ml methylene chloride. The organic phase was washed with 500 ml 50% sodium chloride solution, dried over magnesium sulfate and filtered off. The solvent was evaporated.

Yield: 780 mg yellow oil.

IR (cm−1): 3341, 1793, 1720, 1687, 1587, 1534, 1382

MS (ISP): 337.2 (M+H)+; 359.2 (M+Na)+

II Preparation of diallyl vinyl isooxacephems; Wittig reaction Scheme 1, 1 to 3

EXAMPLE 1

(E)-(6S,7S)-7-Allyloxycarbonylamino-8-oxo-3-[2-oxo-1-(2,2,2-trifluoro-ethyl)-pyrrolidin-3-ylidenmethyl]-4-oxa-1-aza-bicyclo[4.2.0.] oct-2-ene-2-carboxylic acid allyl ester 780 mg (2.5 mmol) (6S,7S)-7-allyloxycarbonylamino-3-formyl-8-oxo-4-oxa-1-aza-bicyclo[4.2.0.] oct-2-ene-2-carboxylic acid allyl ester were dissolved in 30 ml of a 1:1 mixture of ethylenchloride and 1,2-butylenoxide. Then 1.4 g (2.75 mmol) [2-Oxo-1-(2,2,2,-trifluoro-ethyl)-3-pyrrolidinyl]-triphenyl-phosphonium bromide were added. The white suspension was stirred vigorously and warmed to 40° C. The reaction was controlled via thin layer chromatography (eluent: ethyl acetate/n-hexane 1:1, Rf educt: 0.39, Rf product: 0.16). After 3 hours the reaction mixture was diluted with 100 ml methylenechloride. The organic phase was washed with 150 ml of a saturated solution of sodium chloride and dried over magnesium sulfate. The solvent was evaporated and the residue was chromatographed over silica gel using ethyl acetate/n-hexane 1:1 as eluent.

Yield: 950 mg (78%) amorphous solid.

IR (cm−1): 3426, 1779, 1711, 1646, 1566, 1535, 1390

MS (ISP): 486.2 (M+H)+; 503.2 (M+NH4)+ 508.1 (M+Na)+

According to the procedure set forth in the preceding example the following additional compounds were prepared:

EXAMPLE 2

(E)-(6S,7S)-7-Allyloxycarbonylamino-8-oxo-3-[2-oxo-1-phenyl-pyrrolidin-3-ylidenmethyl]4-oxa-1-aza-bicyclo[4.2.0.] oct-2-ene-2-carboxylic acid allyl ester (6S,7S)-7-allyloxycarbonylamino-3-formyl-8-oxo-4-oxa-1-aza-bicyclo[4.2.0.] oct-2-ene-2-carboxylic acid allyl ester was reacted with [2-oxo-1-phenyl)-3-pyrrolidinyl]-triphenylphosphonium bromide.

IR (cm−1): 3436, 1776, 1710, 1640, 1530, 1391, 1309

MS (ISP): 480.2 (M+H)+

EXAMPLE 3

(E)-(6S,7S)-7-Allyloxycarbonylamino-3-[1-(4-nitrobenzyl)-2-oxo-pyrrolidin-3-ylidenemethyl]-8-oxo4-oxa-1-aza-bicyclo[4.2.0.] oct-2-ene-2-carboxylic acid allyl ester (6S,7S)-7-allyloxycarbonylamino-3-formyl-8-oxo-4-oxa-1-aza-bicyclo[4.2.0.] oct-2-ene-2-carboxylic acid allyl ester was reacted with [2-oxo-1-(4-nitrobenzyl)-3-pyrrolidinyl]-triphenylphosphonium bromide.

IR (cm−1): 3423, 1779, 1712, 1522, 1387, 1347

MS (ISP): 539.2 (M+H)+; 556.2 (M+Na)+

EXAMPLE 4

(E)-(6S,7S)-7-Allyloxycarbonylamino-3-[1-cyclopropyl-2-oxo-pyrrolidin-3-ylidenemethyl]-8-oxo-4-oxa-1-aza-bicyclo[4.2.0.] oct-2-ene-2-carboxylic acid allyl ester (6S,7S)-7-allyloxycarbonylamino-3-formyl-8-oxo-4-oxa-1-aza-bicyclo[4.2.0.] oct-2-ene-2-carboxylic acid allyl ester was reacted with [1-(cyclopropyl)-2-oxo-3-pyrrolidinyl]-triphenylphosphonium bromide.

IR (cm$^{-1}$): 3430, 1780, 1712, 1643, 1562, 1388

MS (ISP): 444.4 (M+H)+

EXAMPLE 5

(E)-(6S,7S)-7-Allyloxycarbonylamino-3-(1-isobutyl-2-oxo-pyrrolidin-3-ylidenemethyl)-8-oxo-4-oxa-1-aza-bicyclo[4.2.0.] oct-2-ene-2-carboxylic acid allyl ester (6S,7S)-7-allyloxycarbonylamino-3-formyl-8-oxo-4-oxa-1-aza-bicyclo[4.2.0.] oct-2-ene-2-carboxylic acid allyl ester was reacted with [1-(isobutyl)-2-oxo-3-pyrrolidinyl]-triphenylphosphonium bromide.

IR (cm$^{-1}$): 3496, 1782, 1712, 1643, 1563, 1387, 1252

MS (ISP): 458.4 (M+H)+

EXAMPLE 6

(E)-(6S,7S)-7-Allyloxycarbonylamino-3-[1-(5-methyl-isooxazol-3-yl)-2-oxo-pyrrolidin-3-ylidenemethyl]-8-oxo-4-oxa-1-aza-bicyclo[4.2.0.] oct-2-ene-2-carboxylic acid allyl ester (6S,7S)-7-allyloxycarbonylamino-3-formyl-8-oxo-4-oxa-1-aza-bicyclo[4.2.0.] oct-2-ene-2-carboxylic acid allyl ester was reacted with [1-(5-methyl-isooxazol-3-yl)-2-oxo-3-pyrrolidinyl]-triphenylphosphonium bromide.

IR (cm$^{-1}$): 3403, 1777, 1714, 1644, 1610, 1508, 1385
MS (ISP): 485.2 (M+H)$^+$

EXAMPLE 7

(E)-(6S,7S)-7-Allyloxycarbonylamino-3-[1-(3-nitrophenyl)-2-oxo-pyrrolidin-3-ylidenemethyl]-8-oxo-4-oxa-1-aza-bicyclo[4.2.0.] oct-2-ene-2-carboxylic acid allyl ester (6S,7S)-7-allyloxycarbonylamino-3-formyl-8-oxo-4-oxa-1-aza-bicyclo[4.2.0.] oct-2-ene-2-carboxylic acid allyl ester was reacted with [1-(3-nitrophenyl)-2-oxo-3-pyrrolidinyl]-triphenylphosphonium bromide.

IR (cm$^{-1}$): 3421, 1778, 1710, 1642, 1610, 1560, 1346
MS (ISP): 525.0 (M+H)$^+$; 547.1 (M+Na)$^+$

EXAMPLE 8

(E)-(6S,7S)-7-Allyloxycarbonylamino-3-[1-(2-fluoro-phenyl)-2-oxo-pyrrolidin-3-ylidenemethyl]-8-oxo-1-oxa-1-aza-bicyclo[4.2.0.] oct-2-ene-2-carboxylic acid allyl ester (6S,7S)-7-allyloxycarbonylamino-3-formyl-8-oxo-4-oxa-1-aza-bicyclo[4.2.0.] oct-2-ene-2-carboxylic acid allyl ester was reacted with [1-(2-fluoro-phenyl)-2-oxo-3-pyrrolidinyl]-triphenylphosphonium bromide.

IR (cm$^{-1}$): 3404, 1782, 1711, 1645, 1565, 1533, 1504, 1389
MS (ISP): 498.2 (M+H)$^+$

EXAMPLE 9

(E)-(6S,7S)-7-Allyloxycarbonylamino-3-[2-oxo-1-(2-pyridinyl)-pyrrolidin-3-ylidenemethyl]-8-oxo-4-oxa-1-aza-bicyclo[4.2.0.] oct-2-ene-2-carboxylic acid allyl ester (6S,7S)-7-allyloxycarbonylamino-3-formyl-8-oxo-4-oxa-1-aza-bicyclo[4.2.0.] oct-2-ene-2-carboxylic acid allyl ester was reacted with [1-(2-pyridinyl)-2-oxo-3-pyrrolidinyl]-triphenylphosphonium bromide.

IR (cm$^{-1}$): 3404, 1778, 1712, 1642, 1567, 1528, 1469, 1435, 1386, 1337, 1309, 1242
MS (ISP): 481.3 (M+H)$^+$

EXAMPLE 10

(E)-(6S,7S)-7-Allyloxycarbonylamino-3-[1-(2-methoxy-phenyl)-2-oxo-pyrrolidin-3-ylidenemethyl]-8-oxo-4-oxa-1-aza-bicyclo[4.2.0.] oct-2-ene-2-carboxylic acid allyl ester (6S,7S)-7-allyloxycarbonylamino-3-formyl-8-oxo-4-oxa-1-aza-bicyclo[4.2.0.] oct-2-ene-2-carboxylic acid allyl ester was reacted with [1-(2-methoxy-phenyl)-2-oxo-3-pyrrolidinyl]-triphenylphosphonium bromide.

IR (cm$^{-1}$): 3434, 1781, 1711, 1644, 1562, 1504, 1388, 1253
MS (ISP): 510.2 (M+H)$^+$

EXAMPLE 11

(E)-(6S,7S)-7-Allyloxycarbonylamino-3-[1-(4hydroxy-phenyl)-2-oxo-pyrrolidin-3-ylidenemethyl]-8-oxo-4-oxa-1-aza-bicyclo[4.2.0.] oct-2-ene-2-carboxylic acid allyl ester (6S,7S)-7-allyloxycarbonylamino-3-formyl-8-oxo-4-oxa-1-aza-bicyclo[4.2.0.] oct-2-ene-2-carboxylic acid allyl ester was reacted with [2-oxo-1-(4-tert-butoxycarbonyloxy-phenyl)-3-pyrrolidinyl]-triphenylphosphonium bromide to obtain (E)-(6S,7S)-7-allyloxycarbonylamino-3-[1-(4-tert-butoxycarbonyloxy-phenyl)-2-oxo-pyrrolidin-3-ylidenemethyl]-8-oxo-4-oxa-1-aza-bicyclo[4.2.0.] oct-2-ene-2-carboxylic acid allyl ester.

IR (cm$^{-1}$): 3424, 1761, 1719, 1509, 1392, 1149
MS (ISP): 596.3 (M+H)$^+$ 595 mg (1 mmol) (E)-(6S,7S)-7-allyloxycarbonylamino-3-[1-(4-tert-butoxycarbonyloxy-phenyl)-2-oxo-pyrrolidin-3-ylidenemethyl]-8-oxo-4-oxa-1-aza-bicyclo[4.2.0.] oct-2-ene-2-carboxylic acid allyl ester were dissolved in 2 ml dichloromethane. At 25° C. 2 ml formic acid were added. After 28 hours the solvent was evaporated. The residue was dissolved in a mixture of dichloromethane/methanol (9:1) and washed with water. The organic phase was dried over magnesium sulfate, filtered off and concentrated on a rotary evaporator. The residue was purified by chromatography over silica gel using dichloromethane/methanol (95:5) as eluent.

Yield: 121 mg (24.4%) amorphous solid.
IR (cm$^{-1}$): 3405, 1775, 1709, 1636, 1514, 1391
MS (ISP): 496.1 (M+H)$^+$; 518.0 (M+Na)$^+$ II Liberation of the betaine; Scheme 1, 3 to 4

EXAMPLE 13

(E)-(6S,7S)-7-Amino-8-oxo-3-[2-oxo-1-(2,2,2-trifluoro-ethyl)-pyrrolidin-3-ylidenmethyl]-4-oxa-1-aza-bicyclo[4.2.0.] oct-2-ene-2carboxylic acid 330 mg (0.679 mmol ) (E)-(6S,7S)-7-allyloxycarbonylamino-8-oxo-3-[2-oxo-1-(2,2,2-trifluoro-ethyl)-pyrrolidin-3-ylidenmethyl]-4-oxa-1-aza-bicyclo [4.2.0.] oct-2-ene-2-carboxylic acid allyl ester were dissolved in 15 ml tetrahydrofuran. At room temperature 10 mg (2 mol %, 0.0136 mmol) palladium-bis-(triphenylphosphin)-dichloride and 0.54 ml (3.39 mmol) 2-ethylcaproic acid were added. Within 3 minutes 0.90 ml (988 mg, 3.39 mmol) tributyltinhydride were added dropwise. After 10 minutes yellow crystals were obtained. The suspension was stirred for further two hours and the crystals were filtered off under suction, washed with 20 ml tetrahydrofuran and 30 ml ethyl acetate and dried at high vacuum.

Yield: 220 mg (89%)
IR (cm$^{-1}$): 3433,1773, 1692, 1643, 1565, 1266, 1155
MS (ISP): 362.1 (M+H)$^+$; 384.2 (M+Na)$^+$ According to the procedure set forth in the preceding example the following additional compounds were prepared:

EXAMPLE 14

(E)-(6S,7S)-7-Amino-3-[1-(4-nitro-benzyl)-2-oxo-pyrrolidin-3-ylidenemethyl]-8-oxo-4-oxa-1-aza-bicyclo[4.2.0.] oct-2-ene-2-carboxylic acid Starting from (E)-(6S,7S)-7-allyloxycarbonylamino-3-[1-(4-nitro-benzyl)-2-oxo-pyrrolidin-3-ylidenemethyl]-8-oxo-4-oxa-1-aza-bicyclo [4.2.0.] oct-2-ene-2-carboxylic acid allyl ester.

IR (cm$^{-1}$): 3433,1766, 1679, 1638, 1603, 1520, 1347
MS (ISP): 415.2 (M+H)$^+$

EXAMPLE 15

(E)-(6S,7S)-7-Amino-8-oxo-3-[2-oxo-1-phenyl-pyrrolidin-3-ylidenemethyl]-4-oxa-1-aza-bicyclo [4.2.0.] oct-2-ene-2-carboxylic acid Starting from (E)-(6S,7S)-7-allyloxycarbonylamino-8-oxo-3-[2-oxo-1-phenyl-pyrrolidin-3-ylidenmethyl]-4-oxa-1-aza-bicyclo[4.2.0.] oct-2-ene-2-carboxylic acid allyl ester.

EXAMPLE 16

(E)-(6S,7S)-7-Amino-3-(1-cyclopropyl-2-oxo-pyrrolidin-3-ylidenemethyl)-8-oxo-4-oxa-1-aza-bicyclo[4.2.0.] oct-2-ene-2-carboxylic acid Starting from (E)-(6S,7S)-7-allyloxycarbonylamino-3-[1-cyclopropyl-2-oxo-pyrrolidin-3-ylidenemethyl]-8-oxo-4-oxa-1-aza-bicyclo[4.2.0.] oct-2-ene-2-carboxylic acid allyl ester.

IR (cm$^{-1}$): 3433,1768, 1683, 1638, 1563, 1404, 1364

MS (ISN): 318.3 (M–H)$^-$

EXAMPLE 17

(E)-(6S,7S)-7-Amino-3(1-isobutyl-2-oxo-pyrrolidin-3-ylidenemethyl)-8-oxo-4-oxa-1-aza-bicyclo[4.2.0.] oct-2-ene-2-carboxylic acid Starting from (E)-(6S,7S)-7-allyloxycarbonylamino-3-(1-isobutyl-2-oxo-pyrrolidin-3-ylidenemethyl)-8-oxo-4-oxa-1-aza-bicyclo [4.2.0.] oct-2-ene-2-carboxylic acid allyl ester.

IR (cm$^{-1}$): 3431, 1806, 1771, 1682, 1644, 1558, 1406, 1360

MS (ISN): 334.3 (M–H)$^-$

EXAMPLE 18

(E)-(6S,7S)-7-Amino-3-[1-(5-methyl-isooxazol-3-yl)-2-oxo-pyrrolidin-3-ylidenemethyl]-8-oxo-4-oxa-1-aza-bicyclo[4.2.0.] oct-2-ene-2-carboxylic acid Starting from (E)-(6S,7S)-7-allyloxycarbonylamino-3-[1-(5-methyl-isooxazolyl)-2-oxo-pyrrolidin-3-ylidenemethyl]-8-oxo-4-oxa-1-aza-bicyclo[4.2.0.] oct-2-ene-2-carboxylic acid allyl ester.

IR (cm$^{-1}$): 3436,1799, 1701, 1608, 1508, 1457

MS (ISN): 359.3 (M–H)$^-$; 376.3 (M–H+NH$_3$)$^-$

EXAMPLE 19

(E)-(6S,7S)-7-Amino-3-[1-(3-nitrophenyl)-2-oxo-pyrrolidin-3-ylidenemethyl]-8-oxo-4-oxa-1-aza-bicyclo[4.2.0.] oct-2-ene-2-carboxylic acid Starting from (E)-(6S,7S)-7-allyloxycarbonylamino-3-[1-(3-nitrophenyl)-2-oxo-pyrrolidin-3-ylidenemethyl]-8-oxo-4-oxa-1-aza-bicyclo[4.2.0.] oct-2-ene-2-carboxylic acid allyl ester.

IR (cm$^{-1}$): 3432, 1766, 1689, 1634, 1529, 1394, 1347

MS (ISN): 399.2 (M–H)$^-$; 416.3 (M–H+NH$_3$)$^-$

EXAMPLE 20

(E)-(6S,7S)-7-Amino-3-[1-(4-hydroxyphenyl)-2-oxo-pyrrolidin-3-ylidenemethyl]-8-oxo-4-oxa-1-aza-bicyclo[4.2.0.] oct-2-ene-2-carboxylic acid Starting from (E)-(6S,7S)-7-allyloxycarbonylamino-3-[1-(4-hydroxyphenyl)-2-oxo-pyrrolidin-3-ylidenemethyl]-8-oxo-4-oxa-1-aza-bicyclo[4.2.0.] oct-2-ene-2-carboxylic acid allyl ester.

IR (cm$^{-1}$): 3430,1770, 1679, 1634, 1514, 1401, 1337

MS (ISN): 370.2 (M–H)$^-$

EXAMPLE 21

(E)-(6S,7S)-7-Amino-3-[1-(2-fluoro-phenyl)-2-oxo-pyrrolidin-3-ylidenemethyl]8-oxo-4-oxa-1-aza-bicyclo[4.2.0.] oct-2-ene-2-carboxylic acid Starting from (E)-(6S,7S)-7-allyloxycarbonylamino-3-[1-(2-fluoro-phenyl)-2-oxo-pyrrolidin-3-ylidenemethyl]-8-oxo-4-oxa-1-aza-bicyclo [4.2.0.] oct-2-ene-2-carboxylic acid allyl ester.

IR (cm$^{-1}$): 3432, 1774, 1692, 1638, 1564, 1504, 1400

MS (ISP): 374.2 (M+H)$^+$

EXAMPLE 22

(E)-(6S,7S)-7-Amino-3-[2-oxo-1-(2-pyridinyl)-pyrrolidin-3-ylidenemethyl]-8-oxo-4-oxa-1-aza-bicyclo[4.2.0.] oct-2-ene-2-carboxylic acid Starting from (E)-(6S,7S)-7-allyloxycarbonylamino-3-[2-oxo-1-(2-pyridinyl)-pyrrolidin-3-ylidenemethyl] -8-oxo-4-oxa-1-aza-bicyclo [4.2.0.] oct-2-ene-2-carboxylic acid allyl ester.

IR (cm$^{-1}$): 3434, 1773, 1691, 1635, 1587, 1469, 1436, 1391

MS (ISN): 355.3 (M–H)$^-$; 372.3 (M–H+NH$_3$)$^-$

EXAMPLE 23

(E)-(6S,7S)-7-Amino-3-[1-(2-methoxy-phenyl)-2-oxo-pyrrolidin-3-ylidenemethyl]-8-oxo-4-1-aza-bicyclo[4.2.0.] oct-2-ene-2-carboxylic acid Starting from (E)-(6S,7S)-7-allyloxycarbonylamino-3-[1-(2-methoxyphenyl)-2-oxo-pyrrolidin-3-ylidenemethyl]-8-oxo-4-oxa-1-aza-bicyclo[4.2.0.] oct-2-ene-2-carboxylic acid allyl ester.

IR (cm$^{-1}$): 3434, 1770, 1686, 1636, 1595, 1503, 1400

MS (ISP): 386.2 (M+H)$^+$;

III Acylation of the betaine; Scheme 1, 4 to 5

EXAMPLE 24

(E)-(6S,7S)-7-[(Z)-2-(2-Amino-thiazol-4-yl)-2-cyclopentyloxyimino-acetylamino]-8-oxo-3-[(E)-2-oxo-1-(2,2,2-trifluoro-ethyl)-pyrrolidin-3-ylidenmethyl-]-4-oxa-1-aza-bicyclo[4.2.0.] oct-2-ene-2-carboxylic acid as sodium salt

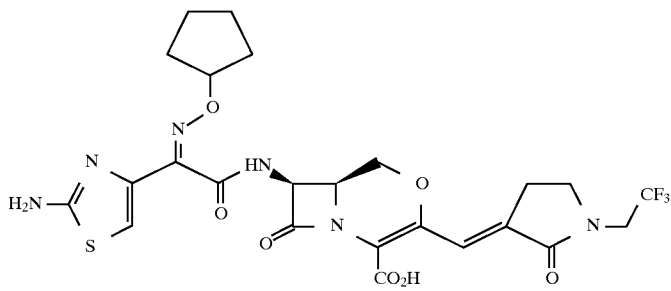

To a suspension of 90 mg (0.25 mmol) (E)-(6S,7S)-7-amino-8-oxo-3-[2-oxo-1-(2,2,2-trifluoro-ethyl)-pyrrolidin-3-ylidenmethyl]-4-oxa-1-aza-bicyclo[4.2.0.] oct-2-ene-2-carboxylic acid in 8 ml dimethylformamide 33 mg (0.27 mmol) (Z)-2-(2-amino-thiazol-4-yl)-2-cyclopentyloxyimino-thioacetic acid-S-benzothiazol-2-yl ester were added at room temperature according to the European Patent Application EPA-0 620 225 or to H. Tsubouchi et al., J. Med. Chem. 1995, 38, 2152–57. The reaction mixture was stirred for 20 hours at room temperature. Dimethylformamide was evaporated. The residue was taken up in 3 ml ethyl acetate. The obtained crystals were filtered off over glass fiber under suction and dissolved in 3 ml dimethylformamide. Then 0.1 ml (0.2 mmol) 2N sodium 2-ethyl-capronate solution were added. The solvent was evaporated, 1.5 ml water were added and the aqueous phase was chromatographed over a polymeric hydrophobic gel (eluent: water-acetonitrile). The fractions containing the product were combined and lyophilized.

Yield: 51 mg (33%) light yellow lyophilizate.

IR ($cm^{-1}$): 3430, 1758, 1668, 1638, 1532, 1392

MS (ISP): 599.3 $(M+H)^+$; 621.2 $(M+Na)^+$

According to the procedure set forth in the preceding example the following additional compounds were prepared:

EXAMPLE 25

(E)-(6S,7S)-7-[(Z)-2-(2-Amino-thiazol-4-yl)-2-cyclopentyloxyimino-acetylamino]-8-oxo-3-[(E)-2-oxo-1-phenyl-pyrrolidin-3-ylidenmethyl]4-oxa-1-aza-bicyclo[4.2.0.] oct-2-ene-2-carboxylic acid as sodium salt

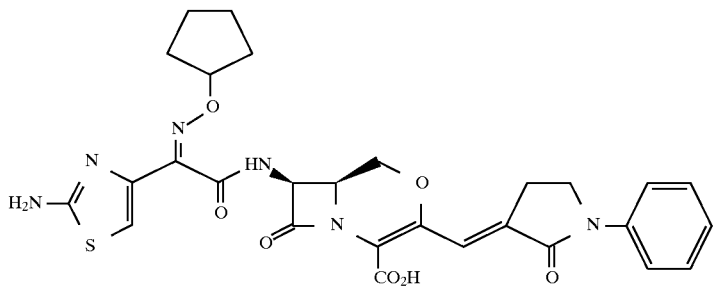

Starting from (E)-(6S,7S)-7-amino-8-oxo-3-[2-oxo-1-phenyl-pyrrolidin-3-ylidenemethyl]-4-oxa-1-aza-bicyclo [4.2.0.] oct-2-ene-2-carboxylic acid and (Z)-2-(2-amino-thiazol-4-yl)-2-cyclopentyloxyimino-thioacetic acid-S-benzothiazol-2-yl ester.

IR ($cm^{-1}$): 3430, 1759, 1668, 1630, 1596, 1532, 1392

MS (ISP): 593.3 $(M+H)^+$

EXAMPLE 26

(E)-(6S,7S)-7-[(Z)-2-(2-Amino-thiazol-4-yl)-2-cyclopentyloxymino-acetylamino]-8-oxo-3-[(E)-1-(4-nitro-benzyl)-2-oxo-pyrrolidin-3-ylidenemethyl]-4-oxa-1-aza-bicyclo[4.2.0.] oct-2-ene-2-carboxylic acid as sodium salt

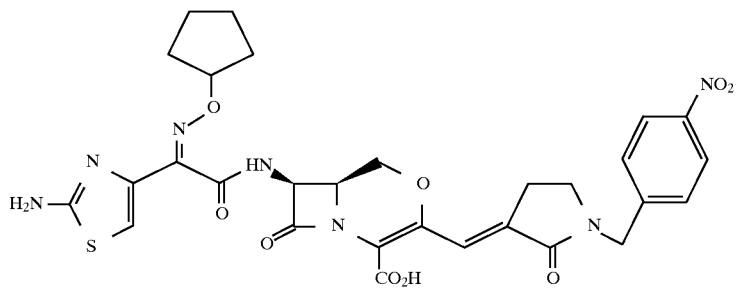

Starting from (E)-(6S,7S)-7-amino-3-[1-(4-nitro-benzyl)-2-oxo-pyrrolidin-3-ylidenemethyl]-8-oxo-4-oxa-1-aza-bicyclo[4.2.0.] oct-2-ene-2-carboxylic acid and (Z)-2-(2-amino-thiazol-4-yl)-2-cyclopentyloxyimino-thioacetic acid-S-benzothiazol-2-yl ester.

IR (cm$^{-1}$): 3427, 1759, 1669, 1636, 1604, 1529, 1390, 1345

MS (ISP): 652.4 (M+H)$^+$; 674.4 (M+Na)$^+$

EXAMPLE 27

(E)-(6S,7S)-7-[(Z)-2-(2-Amino-thiazol-4-yl)-2-cyclopentyloxyimino-acetylamino]-8-oxo-3-[(E)-1-(cyclopropyl)-2-oxo-pyrrolidin-3-ylidenemethyl]4-oxa-1-aza-bicyclo[4.2.0.] oct-2-ene-2-carboxylic acid as sodium salt

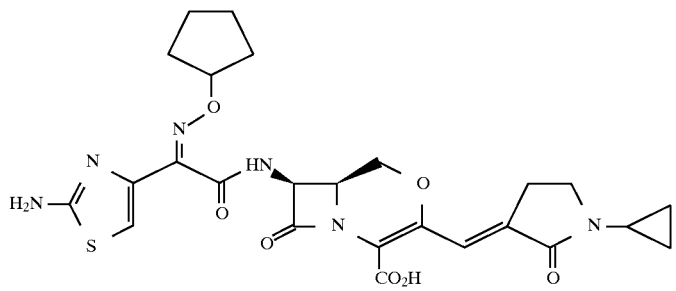

Starting from (E)-(6S,7S)-7-amino-3-(1-cyclopropyl-2-oxo-pyrrolidin-3-ylidenemethyl)-8-oxo-4-oxa-1-aza-bicyclo[4.2.0.] oct-2-ene-2-carboxylic acid and (Z)-2-(2-amino-thiazol-4-yl)-2-cyclopentyloxyimino-thioacetic acid-S-benzothiazol-2-yl ester.

IR (cm$^{-1}$): 3420, 1759, 1665, 1631, 1603, 1532, 1391

MS (ISP): 557.2 (M+2H−Na)$^+$; 579.3 (M+H)$^+$

EXAMPLE 28

(E)-(6S,7S)-7-[(Z)-2-(2-Amino-thiazol-4-yl)-2-cyclopentyloxyimino-acetylamino]-8-oxo-3-[(E)-1-(isobutyl)-2-oxo-pyrrolidin-3-ylidenemethyl]-4-oxa-1-aza-bicyclo[4.2.0.] oct-2-ene-2-carboxylic acid as sodium salt

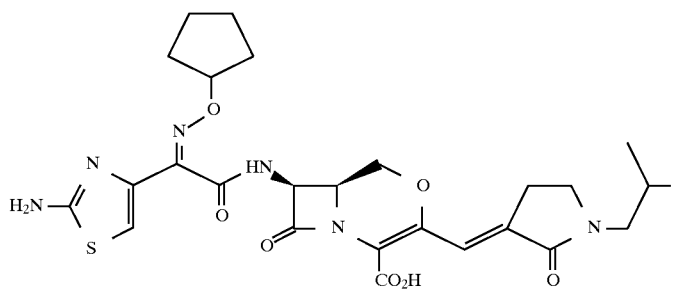

Starting from (E)-(6S,7S)-7-amino-3-(1-isobutyl-2-oxo-pyrrolidin-3-ylidenemethyl)-8-oxo-4-oxa-1-aza-bicyclo[4.2.0.] oct-2-ene-2-carboxylic acid and (Z)-2-(2-amino-thiazol-4-yl)-2-cyclopentyloxyimino-thioacetic acid-S-benzothiazol-2-yl ester.

IR (cm$^{-1}$): 3428, 2959, 1759, 1665, 1635, 1533, 1390

MS (ISP): 573.3 (M+H)$^+$; 595.3 (M+Na)$^+$

EXAMPLE 29

(E)-(6S,7S)-7-[(Z)-2-(2-Amino-thiazol-4-yl)-2-cyclopentyloxyimino-acetylamino]-8-oxo-3-[(E)-1-(5-methyl-isooxazolyl)-2-oxo-pyrrolidin-3-ylidenemethyl]-4-oxa-1-aza-bicyclo[4.2.0] oct-2-ene-2-carboxylic acid as sodium salt

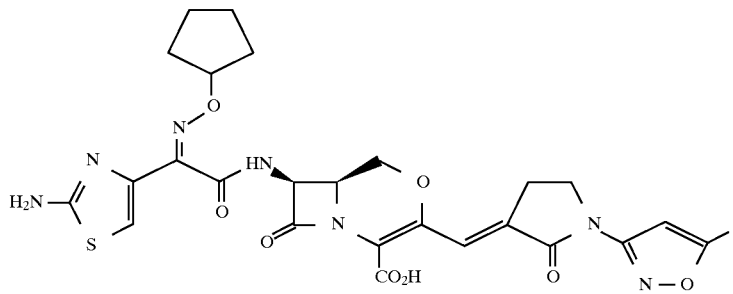

Starting from (E)-(6S,7S)-7-amino-3-[1-(5-methyl-isooxazolyl)-2-oxo-pyrrolidin-3-ylidenemethyl]-8-oxo-4-oxa-1-aza-bicyclo[4.2.0.] oct-2-ene-2-carboxylic acid and (Z)-2-(2-amino-thiazol-4-yl)-2-cyclopentyloxyimino-thioacetic acid-S-benzothiazol-2-yl ester.

IR (cm$^{-1}$): 3418, 1759, 1608, 1506, 1382

MS (ISP): 598.3 (M+2H−Na)$^+$; 620 (M+H)$^+$

EXAMPLE 30

(E)-(6S,7S)-7-[(Z)-2-(2-Amino-thiazol 4-yl)-2-cyclopentyloxyimino-acetylamino]-8-oxo3-[(E)-1-(3-nitrophenyl)-2-oxo-pyrrolidin-3-ylidenemethyl]-4-oxa-1-aza-bicyclo[4.2.0.] oct-2-ene-2-carboxylic acid as sodium salt

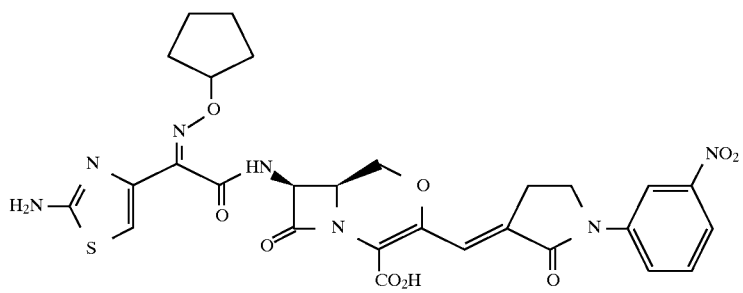

Starting from (E)-(6S,7S)-7-amino-3-[1-(3-nitrophenyl)-2-oxo-pyrrolidin-3-ylidenemethyl]-8-oxo-4-oxa-1-aza-bicyclo [4.2.0.] oct-2-ene-2-carboxylic acid and (Z)-2-(2-amino-thiazol-4-yl)-2-cyclopentyloxyimino-thioacetic acid-S-benzothiazol-2-yl ester.

IR (cm$^{-1}$): 3437, 1758, 1626, 1529, 1388, 1346

MS (ISP): 638.3 (M+2H–Na)$^+$; 660.3 (M+H)$^+$

EXAMPLE 31

(E)-(6S,7S)-7-[(Z)-2-(2-Amino-thiazol4-yl)-2-cyclopentyloxyimino-acetylamino]-8-oxo-3-[(E)-1-(4-hydroxyphenyl)-2-oxo-pyrrolidin-3-ylidenemethyl]-4-oxa-1-aza-bicyclo[4.2.0.] oct-2-ene-2-carboxylic acid as sodium salt

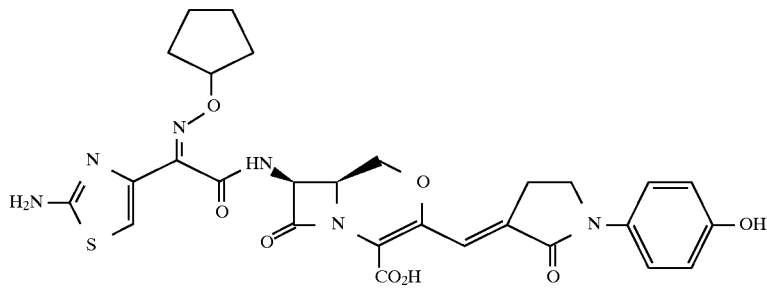

Starting from (E)-(6S,7S)-7-amino-3-[1-(4-hydroxyphenyl)-2-oxo-pyrrolidin-3-ylidenemethyl]-8-oxo-4-oxa-1-aza-bicyclo [4.2.0.] oct-2-ene-2-carboxylic acid and (Z)-2-(2-amino-thiazol-4-yl)-2-cyclopentyloxyimino-thioacetic acid-S-benzothiazol-2-yl ester.

IR (cm$^{-1}$): 3435, 1758, 1629, 1513, 1392

MS (ISP): 609.3 (M+H)$^+$

EXAMPLE 32

(E)-(6S,7S)-7-[(Z)-2-(2-Amino-thiazol4-yl)-2-cyclopentyloxyimino-acetylamino]-3-[(E)-1-(2-fluoro-phenyl)-2-oxo-pyrrolidin-3-ylidenemethyl]-8-oxo-4-oxa-1-aza-bicyclo[4.2.0.] oct-2-ene-2-carboxylic acid as sodium salt

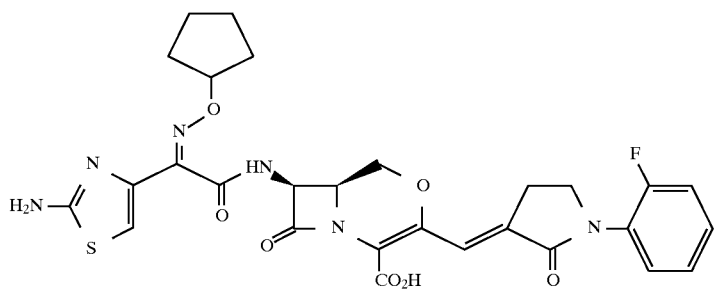

Starting from (E)-(6S,7S)-7-amino-3-[1-(2-fluorophenyl)-2-oxo-pyrrolidin-3-ylidenemethyl]-8-oxo-4-oxa-1-aza-bicyclo[4.2.0.] oct-2-ene-2-carboxylic acid and (Z)-2-(2-amino-thiazol-4-yl)-2-cyclopentyloxyimino-thioacetic acid-S-benzothiazol-2-yl ester.

IR (cm$^{-1}$): 3430, 1757, 1675, 1610, 1530, 1390

MS (ISP): 611.4 (M+H)$^+$

EXAMPLE 33

(E)-(6S,7S)-7-[(Z)-2-(2-Amino-thiazol-4-yl)-2-cyclopentyloxyimino-acetylamino]-3-[2-oxo-1-(2-pyridinyl)-pyrrolidin-3-ylidenemethyl]-8-oxo-4-oxa-1-aza-bicyclo[4.2.0.] oct-2-ene-2-carboxylic acid as sodium salt

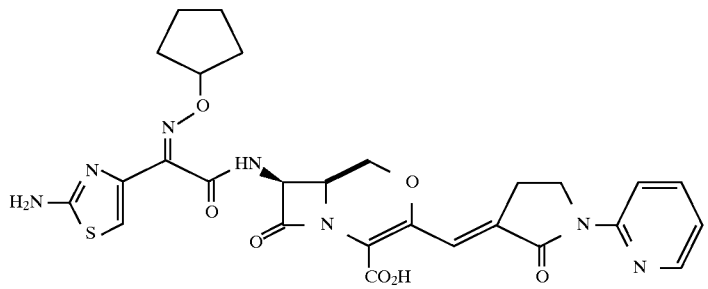

Starting from (E)-(6S,7S)-7-amino-3-[2-oxo-1-(2-pyridinyl)-pyrrolidin-3-ylidenemethyl]-8-oxo-4-oxa-1-aza-bicyclo[4.2.0.] oct-2-ene-2-carboxylic acid IR (cm$^{-1}$): 3439, 1761, 1631, 1586, 1534, 1386

MS (ISP): 616.3 (M+Na)$^+$; 594.4 (M+H)$^+$

EXAMPLE 34

(E)-(6S,7S)-7-[(Z)-2-(2-Amino-thiazol-4-yl)-2-cyclopentyloxyimino-acetylamino]-3-[(E)-1-(1-methyl-pyridinium-2-yl)-2-oxo-pyrrolidin-3-ylidenemethyl]-8-oxo-4-oxa-1-aza-bicyclo[4.2.0.] oct-2-ene-2-carboxylic acid

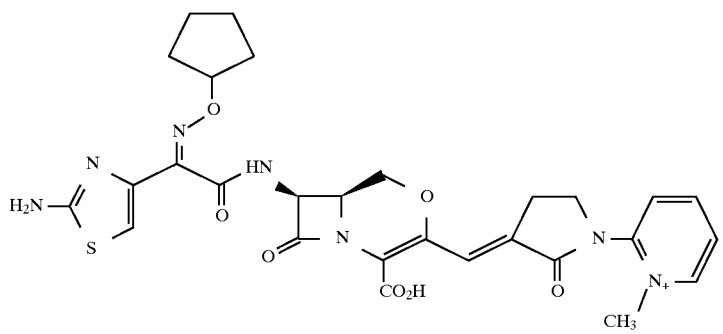

(E)-(6S,7S)-7-[(Z)-2-(2-amino-thiazol-4-yl)-2-cyclopentyloxyimino-acetylamino]-3-[2-oxo-1-(2-pyridinyl)-pyrrolidin-3-ylidenemethyl]-8-oxo-4-oxa-1-aza-bicyclo[4.2.0.] oct-2-ene-2-carboxylic acid (Example 33) was reacted with methyl iodide.

IR (cm$^{-1}$): 3428, 1780, 1686, 1634, 1569, 1382.

MS (ISP): 608.4 (M+H)$^+$

EXAMPLE 35

(E)-(6S,7S)-7-[(Z)-2-(2-Amino-thiazol-1-yl)-2-cyclopentyloxyimino-acetylamino]-3-[1-(2-methoxy-phenyl)-2-oxo-pyrrolidin-3-ylidenemethyl]-8-oxo-4-oxa-1-aza-bicyclo[4.2.0.] oct-2-ene-2-carboxylic acid as sodium salt

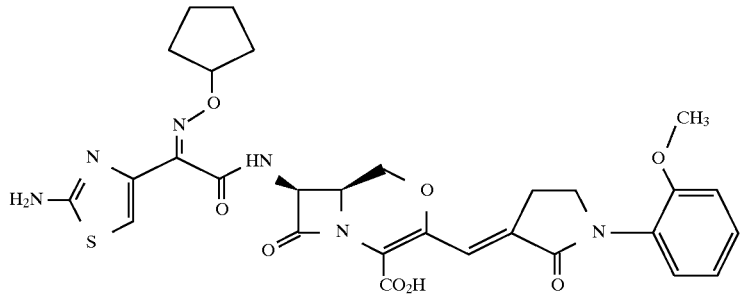

Starting from (E)-(6S,7S)-7-amino-3-[1-(2-methoxy-phenyl)-2-oxo-pyrrolidin-3-ylidenemethyl]-8-oxo-4-oxa-1-aza-bicyclo [4.2.0.] oct-2-ene-2-carboxylic acid.

IR (cm$^{-1}$): 1758, 1672, 1601, 1503, 1390.

MS (ISP): 623.5 (M+H)$^+$

EXAMPLE 36

(E)-(6S,7S)-7-[(Z)-2-(2-Amino-thiazol-4-yl)-2-carbamoylmethoxyimino-acetylamino]-3-[(E)-1-(4nitro-benzyl)-2-oxo-pyrrolidin-3-ylidenemethyl]-8-oxo-4-oxa-1-aza-bicyclo[4.2.0.] oct-2-ene-2-carboxylic acid as sodium salt

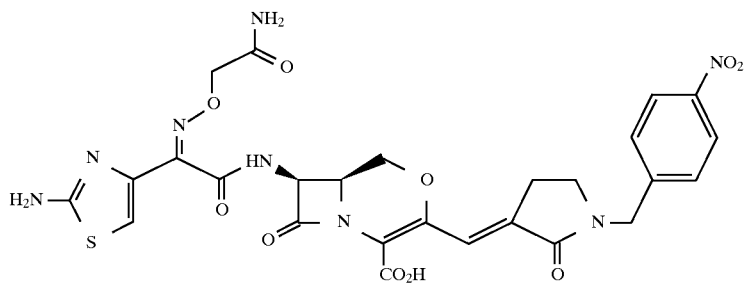

Starting from (E)-(6S,7S)-7-amino-3-[1-(4-nitro-benzyl)-2-oxo-pyrrolidin-3-ylidenemethyl]-8-oxo-4-oxa-1-aza-bicyclo[4.2.0.] oct-2-ene-2-carboxylic acid and (Z)-2-(2-amino-thiazol-4-yl)-2-carbamoylmethoxyimino-thioacetic acid-S-benzothiazol-2-yl ester.

IR (cm$^{-1}$): 3429, 1759, 1672, 1634, 1603, 1522, 1390, 1346

MS (ISP): 641.3 (M+H)$^+$; 663.3 (M+Na)$^+$

EXAMPLE 37

(E)-(6S,7S)-7-[(Z)-2-(2-Amino-thiazol-4-yl)-2-carbamoylmethoxyimino-acetylamino]-3-[(E)-1-(phenyl)-2-oxo-pyrrolidin-3-ylidenemethyl]-8-oxo-4-oxa-1-aza-bicyclo[4.2.0.] oct-2-ene-2-carboxylic acid as sodium salt

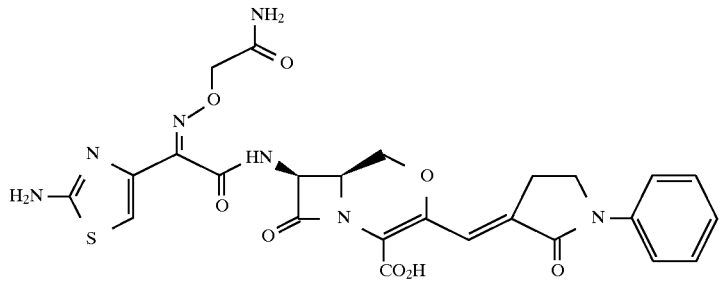

Starting from (E)-(6S,7S)-7-amino-8-oxo-3-[2-oxo-1-phenyl-pyrrolidin-3-ylidenemethyl]-4-oxa-1-aza-bicyclo[4.2.0.] oct-2-ene-2-carboxylic acid and (Z)-2-(2-amino-thiazol-4-yl)-2-carbamoylmethoxyimino-thioacetic acid-S-benzothiazol-2-yl ester.

IR (cm$^{-1}$): 3429, 1757, 1674, 1629, 1594, 1533, 1390

MS (ISP): 582.3 (M+H)$^+$; 604.2 (M+Na)$^+$

EXAMPLE 38

(E)-(6S,7S)-7-[(Z)-2-(2-Amino-thiazol-4-yl)-2-carbamoyhmethoxyimino-acetylamino]-3-[(E)-1-cyclopropyl-2-oxo-pyrrolidin-3-ylidenemethyl]-8-oxo-4-oxa-1-aza-bicyclo[4.2.0.] oct-2-ene-2-carboxylic acid as sodium salt.

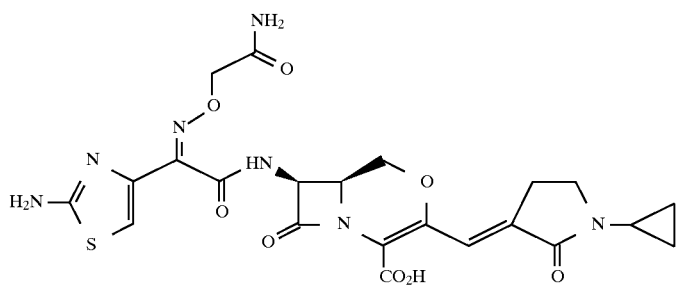

Starting from (E)-(6S,7S)-7-amino-3-(1-cyclopropyl-2-oxo-pyrrolidin-3-ylidenemethyl)-8-oxo-4-oxa-1-aza-bicyclo[4.2.0.] oct-2-ene-2-carboxylic acid and (Z)-2-(2-amino-thiazol-4-yl)-2-carbamoylmethoxyimino-thioacetic acid-S-benzothiazol-2-yl ester.

IR (cm$^{-1}$): 3426, 3199, 1758, 1672, 1630, 1563, 1535, 1392

MS (ISP): 546.2 (M+H)+; 568.2 (M+Na)$^+$

EXAMPLE 39

(E)-(6S,7S)-7-[(Z)-2-(2-Amino-thiazol-4-yl)-2-carbamoylmethoxyimino-acetylamino]-3-[(E)-1-(5-methyl-isooxazolyl)-2-oxo-pyrrolidin-3-ylidenemethyl]-8-oxo-4-oxa-1-aza-bicyclo[4.2.0.] oct-2-ene-2-carboxylic acid as sodium salt

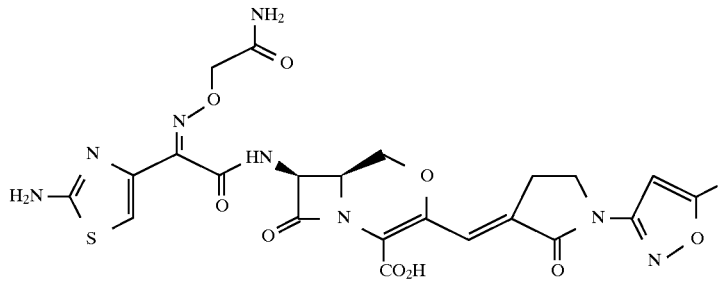

Starting from (E)-(6S,7S)-7-amino-3-[1-(5-methyl-isooxazolyl)-2-oxo-pyrrolidin-3-ylidenemethyl]-8-oxo-4-oxa-1-aza-bicyclo [4.2.0.] oct-2-ene-2-carboxylic acid and (Z)-2-(2-amino-thiazol-4-yl)-2-carbamoylmethoxyimino-thioacetic acid-S-benzothiazol-2-yl ester.

IR (cm$^{-1}$): 3432, 3197, 1760, 1679, 1608, 1562, 1534, 1506, 1385

MS (ISP): 587.2 (M+H)$^+$; 609.2 (M+Na)$^+$

EXAMPLE 40

(E)-(6S,7S)-7-[(Z)-2-(2-Amino-thiazol-4-yl)-2-carbamoylmethoxyimino-acetylamino]-3-[(E)-1-isobutyl-2-oxo-pyrrolidin-3-ylidenemethyl]-8-oxo-4-oxa-1-aza-bicyclo[4.2.0.] oct-2-ene-2-carboxylic acid as sodium salt

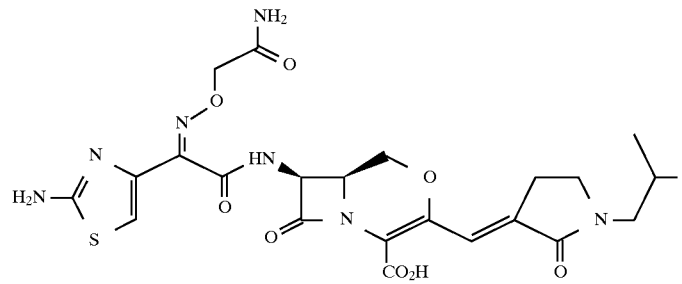

Starting from (E)-(6S,7S)-7-amino-3-(1-isobutyl-2-oxo-pyrrolidin-3-ylidenemethyl)-8-oxo-4-oxa-1-aza-bicyclo [4.2.0.] oct-2-ene-2-carboxylic acid and (Z)-2-(2-amino-thiazol-4-yl)-2-carbamoylmethoxyimino-thioacetic acid-S-benzothiazol-2-yl ester IR (cm$^{-1}$): 3424, 3196, 1758, 1672, 1634, 1534, 1390
MS (ISP): 562.2 (M+H)$^+$; 584.3 (M+Na+H)$^+$

EXAMPLE 41

(E)-(6S,7S)-7-[(Z)-2-(2-Amino-thiazol-4-yl)-2-carbamoylmethoxyimino-acetylamino]-3-[(E)-1-(3-nitrophenyl)-2-oxo-pyrrolidin-3-ylidenemethyl]-8-oxo-4-oxa-1-aza-bicyclo[4.2.0.] oct-2-ene-2-carboxylic acid as sodium salt

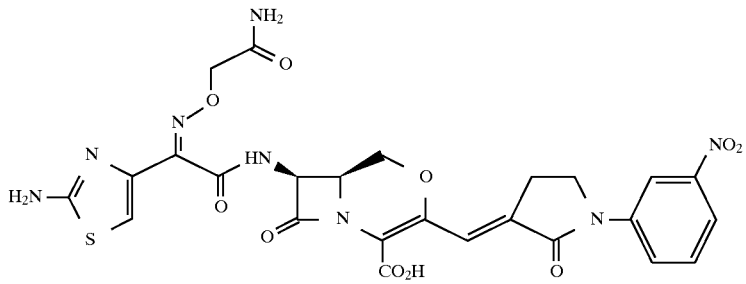

Starting from (E)-(6S,7S)-7-amino-3-[(3-nitrophenyl)-2-oxo-pyrrolidin-3-ylidenemethyl]-8-oxo-4-oxa-1-aza-bicyclo[4.2.0.] oct-2-ene-2-carboxylic acid and (Z)-2-(2-amino-thiazol-4-yl)-2-carbamoylmethoxyimino-thioacetic acid-S-benzothiazol-2-yl ester IR (cm$^{-1}$): 3437, 1759, 1675, 1632, 1529, 1345
MS (ISP): 649.2 (M+H)$^+$; 671.3 (M+Na)$^+$

EXAMPLE 42

(E)-(6S,7S)-7-[(Z)-2-(2-Amino-thiazol-4-yl)-2-hydroxyimino-acetylamino]-8-oxo-3-[(E)-1-(2-methoxy-phenyl)-2-oxo-pyrrolidin-3-ylidenemethyl]-4-oxa-1-aza-bicyclo[4.2.0.] oct-2-ene-2-carboxylic acid as sodium salt

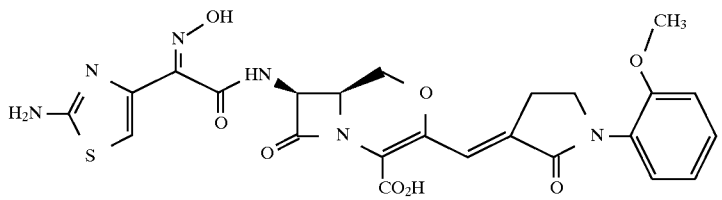

To a suspension of 200 mg (0.519 mmol) (E)-(6S,7S)-7-amino-8-oxo-3-[2-oxo-1-(2-methoxy-phenyl)-2-oxo-pyrrolidin-3-ylidenmethyl-4-oxa-1-aza-bicyclo[4.2.0.] oct-2-ene-2-carboxylic acid in 8 ml dimethylacetamide (Z)-2-(2-amino-thiazol-4-yl)-2-trityloxyimino-acetic acid-benzotriazol-1-yl ester was added at room temperature according to the Journal of Antibiotics, Vol XLIII, p 1564, 1990. The reaction mixture was stirred for 20 hours at room temperature. Dimethylformamide was evaporated. The residue was taken up in 150 ml ethyl acetate/water (1:1). The organic phase was separated and extracted three times with water (50 ml) and dried over magnesium sulfate. The solvent was evaporated and the residue was taken up in ethyl acetate/n-hexane. (E)-(6S,7S)-7-[(Z)-2-(2-Amino-thiazol-4-yl)-2-trityloxyimino-acetylamino]-8-oxo-3-[(E)-1-(2-methoxy-phenyl)-2-oxo-pyrrolidin-3-ylidenemethyl]-4-oxa-1-aza-bicyclo[4.2.0.] oct-2-ene-2-carboxylic acid was obtained.

Yield: 204 mg (49%) light yellow crystals.
IR (cm$^{-1}$): 3437, 1775, 1677, 1635, 1503, 1395
MS (ISP): 797.5 (M+H)$^+$; 814.5 (M+NH$_4$)$^+$ 204 mg (0.255 mmol) (E)-(6S,7S)-7-[(Z)-2-(2-amino-thiazol-4-yl)-2-trityloxyimino-acetylamino]-8-oxo-3-[(E)-1-(2-methoxy-phenyl)-2-oxo-pyrrolidin-3-ylidenemethyl]-4-oxa-1-aza-bicyclo[4.2.0.] oct-2-ene-2-carboxylic acid were dissolved in 1 ml formic acid at room temperature. After 1 hour formic acid was removed in vacuum at 20° C. The residue was taken up in 100 ml diethylether. The obtained crystals were filtered off over glass fiber under suction and dissolved in 3 ml dimethylformamide. Then 0.2 ml (0.4 mmol) 2N sodium 2-ethyl-capronate solution were added. The solvent was evaporated, 3 ml water were added and the aqueous phase was chromatographed over a polymeric hydrophobic gel (eluent: water-acetonitrile). The fractions containing the product were combined and lyophilized.

Yield: 50 mg (34%) light yellow lyophilizate.
IR (cm$^{-1}$): 3430, 1758, 1666, 1630, 1532, 1503, 1391.
MS (ISP): 555.2 (M+H)$^+$; 572.4 (M+NH$_4$)$^+$ 577.3 (M+Na)$^+$

EXAMPLE 43

(E)-(6S,7S)-7-[(Z)-2-(2-Amino-thiazol-4-yl)-2-hydroxyimino-acetylamino]-8-oxo-3-[(E)-1-(isobutyl)-2-oxo-pyrrolidin-3-ylidenemethyl]-4-oxa-1-aza-bicyclo[4.2.0.] oct-2-ene-2-carboxylic acid as sodium salt

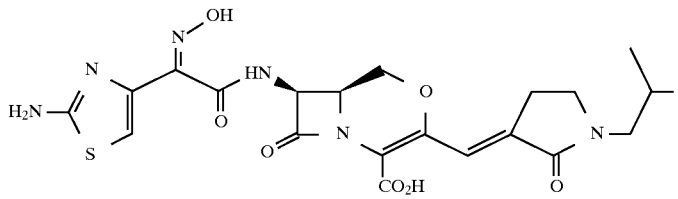

(E)-(6S,7S)-7-[(Z)-2-(2-Amino-thiazol-4-yl)-2-trityloxyimino-acetylamino]-8-oxo-3-[(E)-1-(isobutyl)-2-oxo-pyrrolidin-3-ylidenemethyl]-4-oxa-1-aza-bicyclo[4.2.0.] oct-2-ene-2-carboxylic acid was prepared by reacting (E)-(6S,7S)-7-amino-3-(1-isobutyl-2-oxo-pyrrolidin-3-ylidenemethyl)-8-oxo-4-oxa-1-aza-bicyclo[4.2.0.] oct-2-ene-2-carboxylic acid and (Z)-2-(2-amino-thiazol-4-yl)-2-trityloxyimino-acetic acid-benzotriazol-1-yl ester.

IR (cm$^{-1}$): 3434, 1778, 1676, 1635, 1565, 1532, 1334.

MS (ISP): 747.5 (M+H)$^+$; 764.5 (M+NH$_4$)$^+$ 769,5 (M+Na)$^+$

The trityl-protecting group was cleaved off to give (E)-(6S,7S)-7-[(Z)-2-(2-Amino-thiazol-4-yl)-2-hydroxyimino-acetylamino]-8-oxo-3-[(E)-1-(isobutyl)-2-oxo-pyrrolidin-3-ylidenemethyl]-4-oxa-1-aza-bicyclo[4.2.0.] oct-2-ene-2-carboxylic acid sodium salt.

IR (cm$^{-1}$): 3429, 1757, 1664, 1632, 1534, 1390

MS (ISP): 505.2 (M+H)$^+$; 522.2 (M+NH$_4$)$^+$; 527.2 (M+Na)$^+$

EXAMPLE 44

(E)-(6S,7S)-7-[(Z)-2-(2-Amino-thiazol-4-yl)-2-hydroxyimino-acetylamino]-8-oxo-3-[(E)-1-(2-fluoro-phenyl)-2-oxo-pyrrolidin-3-ylidenemethyl]-4-oxa-1-aza-bicyclo[4.2.0.] oct-2-ene-2-carboxylic acid as sodium salt

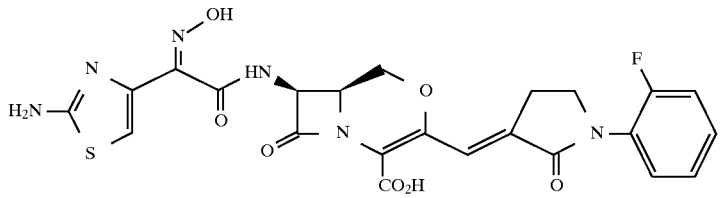

(E)-(6S,7S)-7-[(Z)-2-(2-amino-thiazol-4-yl)-2-trityloxyimino-acetylamino]-8-oxo-3-[(E)-1-(2-fluoro-phenyl)-2-oxo-pyrrolidin-3-ylidenemethyl]-4-oxa-1-aza-bicyclo[4.2.0.] oct-2-ene-2-carboxylic acid was prepared by reacting (E)-(6S,7S)-7-amino-3-[1-(2-fluoro-phenyl)-2-oxo-pyrrolidin-3-ylidenemethyl]-8-oxo-4-oxa-1-aza-bicyclo[4.2.0.] oct-2-ene-2-carboxylic acid with (Z)-2-(2-amino-thiazol-4-yl)-2-trityloxyimino-acetic acid-benzotriazol-1-yl ester.

IR (cm$^{-1}$): 3435, 1777, 1682, 1633, 1503, 1397

MS (ISP): 785.4 (M+H)$^+$; 807.4 (M+Na)$^+$

The trityl-protecting group was cleaved off to give (E)-(6S,7S)-7-[(Z)-2-(2-amino-thiazol-4-yl)-2-hydroxyimino-acetylamino]-8-oxo-3-[(E)-1-(2-fluoro-phenyl)-2-oxo-pyrrolidin-3-ylidenemethyl]-4-oxa-1-aza-bicyclo[4.2.0.] oct-2-ene-2-carboxylic acid sodium salt.

IR (cm$^{-1}$): 3422, 1758, 1669, 1609, 1532, 1504, 1392.

MS (ISP): 543.1 (M+H)$^+$; 560.2 (M+NH$_4$)$^+$

EXAMPLE 45

(E)-(6S,7S)-7-[(Z)-2-(2-Amino-thiazol-4-yl)-2-hydroxyimino-acetylamino]-8-oxo-3-[(E)-1(3-nitro-phenyl)-2-oxo-pyrrolidin-3-ylidenemethyl]-4-oxa-1-aza-bicyclo[4.2.0.] oct-2-ene-2-carboxylic acid as sodium salt

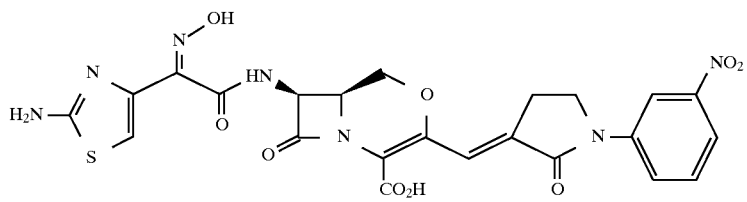

(E)-(6S,7S)-7-[(Z)-2-(2-amino-thiazol-4-yl)-2-trityloxyimino-acetylamino]-8-oxo-3-[(E)-1-(3-nitro-phenyl)-2-oxo-pyrrolidin-3-ylidenemethyl]-4-oxa- 1-aza-bicyclo[4.2.0.] oct-2-ene-2-carboxylic acid was prepared by reacting (E)-(6S,7S)-7-amino-3-[1-(3-nitrophenyl)-2-oxo-pyrrolidin-3-ylidenemethyl]-8-oxo-4-oxa-1-aza-bicyclo [4.2.0.] oct-2-ene-2-carboxylic acid with (Z)-2-(2-amino-thiazol-4-yl)-2-trityloxyimino-acetic acid-benzotriazol-1-yl ester.

IR (cm$^{-1}$): 3437, 1758, 1626, 1529, 1388,1346.

MS (ISP): 812.4 (M+H)$^+$; 829.4 (M+NH$_4$)$^+$; 834.3 (M+Na)$^+$

The trityl-protecting group was cleaved off to give (E)-(6S,7S)-7-[(Z)-2-(2-amino-thiazol-4-yl)-2-hydroxyimino-acetylamino]-8-oxo-3-[(E)-1-(3-nitro-phenyl)-2-oxo-pyrrolidin-3-ylidenemethyl]-4-oxa-1-aza-bicyclo[4.2.0.] oct-2-ene-2-carboxylic acid sodium salt.

IR (cm$^{-1}$): 3434, 1758, 1668, 1617, 1529, 1388.

MS (ISP): 570.2 (M+H)$^+$; 587.3 (M+NH$_4$)$^+$; 592.2 (M+Na)$^+$

EXAMPLE 46

(E)-(6S,7S)-7-[(Z)-2-(2-Amino-thiazol-4-yl)-2-hydroxyimino-acetylamino]-8-oxo-3-[(E)-1-(pyridin-2-yl)-2-oxo-pyrrolidin-3-ylidenemethyl]-4-oxa-1-aza-bicyclo[4.2.0.] oct-2-ene-2-carboxylic acid as sodium salt.

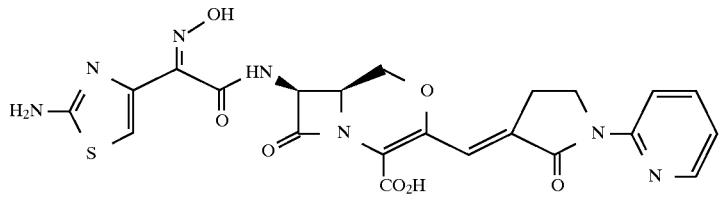

(E)-(6S,7S)-7-[(Z)-2-(2-amino-thiazol-4-yl)-2-trityloxyimino-acetylamino]-8-oxo-3-[(E)-1-(pyridin-2-yl)-2-oxo-pyrrolidin-3-ylidenemethyl]-4-oxa-1-aza-bicyclo [4.2.0.] oct-2-ene-2-carboxylic acid was prepared by reacting (E)-(6S,7S)-7-amino-3-[1-(pyridin-2-yl)-2-oxo-pyrrolidin-3-ylidenemethyl]-8-oxo-4-oxa-1-aza-bicyclo [4.2.0.] oct-2-ene-2-carboxylic acid with (Z)-2-(2-amino-thiazol-4-yl)-2-trityloxyimino-acetic acid-benzotriazol-1-yl ester.

IR (cm$^{-1}$): 3430, 1775, 1684, 1630, 1532, 1389,1309.

MS (ISP): 768.4 (M+H)$^+$; 790.4 (M+Na)$^+$

The trityl-protecting group was cleaved off to give (E)-(6S,7S)-7-[(Z)-2-(2-Amino-thiazol-4-yl)-2-hydroxyimino-acetylamino]-8-oxo-3-[(E)-1-(pyridin-2-yl)-2-oxo-pyrrolidin-3-ylidenemethyl]-4-oxa-1-aza-bicyclo[4.2.0.] oct-2-ene-2-carboxylic acid sodium salt.

IR (cm$^{-1}$): 3427, 1758, 1666, 1628, 1533, 1386.

MS (ISP): 526.1(M+H)$^+$

EXAMPLE 47

(E)-(6S,7S)-7-[(Z)-2-(2-Amino-thiazol-4-yl)-2-hydroxyimino-acetylamino]-8-oxo-3-[(E)-1-(4-nitro-benzyl)-2-oxo-pyrrolidin-3-ylidenemethyl]-4-oxa-1-aza-bicyclo[4.2.0.] oct-2-ene-2-carboxylic acid as sodium salt.

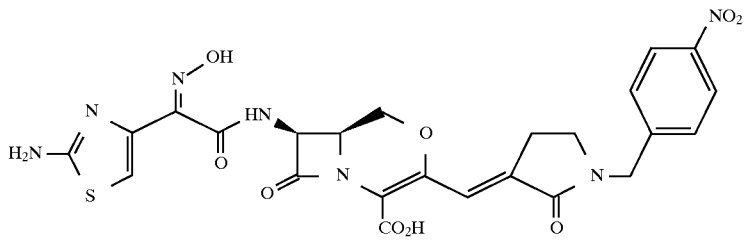

(E)-(6S,7S)-7-[(Z)-2-(2-amino-thiazol-4-yl)-2-trityloxyimino-acetylamino]-8-oxo-3-[(E)-1-(4-nitro-benzyl)-2-oxo-pyrrolidin-3-ylidenemethyl]-4-oxa-1-aza-bicyclo[4.2.0.] oct-2-ene-2-carboxylic acid was prepared by reacting (E)-(6S,7S)-7-amino-3-[1-(4-nitro-benzyl)-2-oxo-pyrrolidin-3-ylidenemethyl]-8-oxo-4-oxa-1-aza-bicyclo [4.2.0.] oct-2-ene-2-carboxylic acid with (Z)-2-(2-amino-thiazol-4-yl)-2-trityloxyimino-acetic acid-benzotriazol-1-yl ester.

IR (cm$^{-1}$): 3435, 1778, 1678, 1636, 1522, 1346.

MS (ISP): 826.5(M+H)$^+$; 843.5 (M+NH$_4$)$^+$; 848.4 (M+Na)$^+$

The trityl-protecting group was cleaved off to give (E)-(6S,7S)-7-[(Z)-2-(2-amino-thiazol-4-yl)-2-hydroxyimino-acetylamino]-8-oxo-3-[(E)-1-(4-nitro-benzyl)-2-oxo-pyrrolidin-3-ylidenemethyl]-4-oxa-1-aza-bicyclo [4.2.0.] oct-2-ene-2-carboxylic acid sodium salt.

IR (cm$^{-1}$): 3430, 1756, 1665, 1633, 1521, 1346.

MS (ISP): 584.3(M+H)$^+$

EXAMPLE 48

(E)-(6S,7S)-7-[(Z)-2-(2-Amino-thiazol-4-yl)-2-hydroxyimino-acetylamino]-8-oxo-3-[(E)-1-(5-methyl-isooxazolyl)-2-oxo-pyrrolidin-3-ylidenemethyl]-4-oxa-1-aza-bicyclo[4.2.0.] oct-2-ene-2-carboxylic acid as sodium salt.

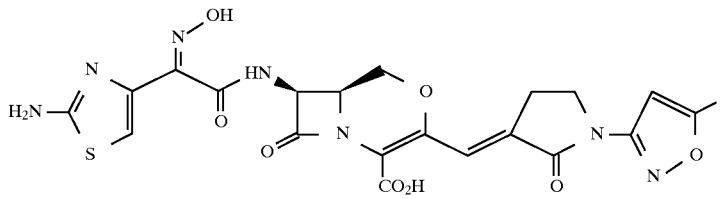

(E)-(6S,7S)-7-[(Z)-2-(2-amino-thiazol-4-yl)-2-trityloxyimino-acetylamino]-8-oxo-3-[(E)-1-(5-methyl-isooxazolyl)-2-oxo-pyrrolidin-3-ylidenemethyl]-4-oxa-1-aza-bicyclo[4.2.0.] oct-2-ene-2-carboxylic acid was prepared by reacting (E)-(6S,7S)-7-amino-3-[1-(5-methyl-isooxazolyl)-2-oxo-pyrrolidin-3-ylidenemethyl]-8-oxo-4-oxa-1-aza-bicyclo[4.2.0.] oct-2-ene-2-carboxylic acid with (Z)-2-(2-amino-thiazol-4-yl)-2-trityloxyimino-acetic acid-benzotriazol-1-yl ester.

IR (cm$^{-1}$): 3435, 1776, 1685, 1609, 1505, 1386.

MS (ISP): 772.4(M+H)$^+$; 794.3 (M+Na)$^+$

The trityl-protecting group was cleaved off to give (E)-(6S,7S)-7-[(Z)-2-(2-amino-thiazol-4-yl)-2-hydroxyimino-acetylamino]-8-oxo-3-[(E)-1-(5-methyl-isooxazolyl)-2-oxo-pyrrolidin-3-ylidenemethyl]-4-oxa-1-aza-bicyclo [4.2.0.] oct-2-ene-2-carboxylic acid sodium salt.

IR (cm$^{-1}$): 3435, 1758, 1609, 1506, 1384.

MS (ISP):530.1(M+H)$^+$; 552.2 (M+Na)$^+$

EXAMPLE 49

(E)-(6S,7S)-7-[[3-(2,6-Dichloro-phenyl)-5methyl-isoxazol-4-yl-carbonyl]-amino]-3-[(E)-1-(isobutyl)-2-oxo-pyrrolidin-3-ylidenemethyl]-4-oxa-1-aza-bicyclo[4.2.0.] oct-2-ene-2-carboxylic acid as sodium salt.

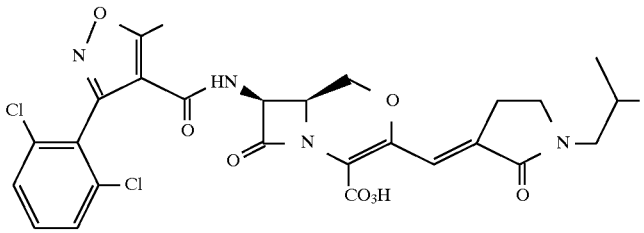

5.02 g (18.45 mmol) 3-(2,6-dichloro-phenyl)-5-methyl-isoxazole-4-carboxylic acid (CAS Reg. No 3919-76-4, Beilstein 5-27, 6-27) were dissolved in 140 ml acetonitrile. 2.8 g (27.6 mmol) N-methyl-morpholine were added. Then 7.36 g 2,2'-dithiobisbenzothiazole were added. A solution of 5.36 g (32.3 mmol) triethylphosphite in 15 ml acetonitrile were added dropwise within two hours at 0° C. The solution was cooled to −10° C. The obtained crystals were filtered off under suction, washed with acetonitrile and ether. 3-(2,6-dichlorophenyl)-5-methyl-isoxazole-4-carbothioic acid S-benzothiazol-2-yl ester was obtained.

Yield: 6.59 g(84.7%)

IR (cm$^{-1}$): 3436, 1669, 1575, 1425

MS (E.I.+QI)=420 (M.)

(E)-(6S,7S)-7-[[3-(2,6-dichloro-phenyl)-5-methyl-isoxazol-4-yl-carbonyl]-amino]-3-[(E)-1-isobutyl-2-oxo-pyrrolidin-3-ylidenemethyl]-8-oxo-4-oxa-1-aza-bicyclo [4.2.0.] oct-2-ene-2-carboxylic acid sodium salt was prepared by reacting (E)-(6S,7S)-7-amino-3-(1-isobutyl-2-oxo-pyrrolidin-3-ylidenemethyl)-8-oxo-4-oxa-1-aza-bicyclo [4.2.0.] oct-2-ene-2-carboxylic acid with 3-(2,6-dichloro-phenyl)-5-methyl-isoxazol-4-carbothioic acid S-benzothiazol-2-yl ester.

IR (cm$^{-1}$): 3429, 1761, 1667, 1601, 1561, 139 1.

MS (ISP): 589.2, 591.2(M+H)$^+$; 606.2, 608.2 (M+NH$_4$)$^+$; 611.2, 613.2 (M+Na)$^+$

EXAMPLE 50

(6S,7S)-3-((E)-1-Isobutyl-2-oxo-pyrrolidin-3-ylidenemethyl)-7[2-(1-methyl-1H-tetrazol-5-ylsulfanyl)-acetylamino)-8-oxo-4-oxa-1-aza-bicyclo [4.2.0.] oct-2-ene-2-carboxylic acid as sodium salt.

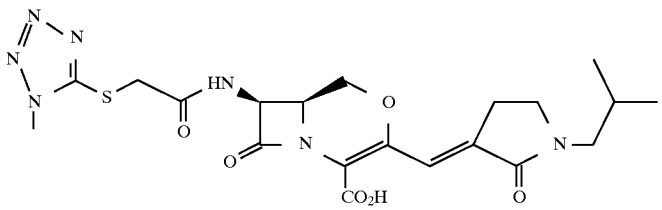

5.2 g (885 mmol) (1-methyl-1H-tetrazol-5-ylsulfanyl)-acetic acid (CAS Reg. No 55862-52-7; Saito, Seiki et al, Synlett (1993), 2, 139–40 ; 29) were dissolved in 100 ml dimetylformamide. Then 3.44 g (32.84 mmol) N-hydroxysuccinimide were added. Then 6.78 g N,N'-dicyclohexylcarbodiimid were added. After a few minutes white crystals were obtained. The suspension was stirred for further five days. The crystals were filtered off. Dimethylformamide was removed in vacuum. The residue was taken up in 60 ml ethyl acetate at 60° C., filtered off, washed with 30 ml ethylacetate (three times) and dried at high vacuum. 1-Methyl-1H-tetrazol-5-ylsulfanyl)-acetic acid 2,5-dioxopyrrolidin-1-yl ester was obtained.

Yield: 6.54 g (80.7%)

IR (cm$^{-1}$): 3497, 1740, 1627, 1415, 1199

MS (E.I.+QI)=272 (M+H)$^+$ (6S,7S)-3-((E)-1-isobutyl-2-oxo-pyrrolidin-3-ylidenemethyl)-7[2-(1-methyl-1H-tetrazol-5-ylsulfanyl)-acetylamino)-8-oxo-4-oxa-1-aza-bicyclo[4.2.0.] oct-2-ene-2-carboxylic acid sodium salt was prepared by reacting (E)-(6S,7S)-7-amino-3-(1-isobutyl-2-oxo-pyrrolidin-3-ylidenemethyl)-8-oxo-4-oxa-1-aza-bicyclo[4.2.0.] oct-2-ene-2-carboxylic acid with (1-methyl-1H-tetrazol-5-ylsulfanyl)-acetic acid 2,5-dioxo-pyrrolidin-1-yl ester.

IR (cm$^{-1}$): 3434, 1759, 1677, 1641, 1597, 1393.

MS (ISP): 492.2(M+H)$^+$; 509.1 (M+NH$_4$)$^+$; 514.0(M+Na)$^+$

EXAMPLE 51

(6S,7S)-7-Acetylamino-3-((E)-1-isobutyl-2-oxo-pyrrolidin-3-ylidenemethyl)-8-oxo-4-oxa-1-aza-bicyclo[4.2.0.] oct-2-ene-2-carboxylic acid as sodium salt (E)-(6S,7S)-7-amino-3-(1-isobutyl-2-oxo-pyrrolidin-3-ylidenemethyl)-8-oxo-4-oxa-1-aza-bicyclo[4.2.0.] oct-2-ene-2-carboxylic acid was reacted with acetanhydride.

IR (cm$^{-1}$): 3439, 1760, 1674, 1640, 1599, 1556, 1392.

MS (ISP): 378.2(M+H)$^+$; 395.3 (M+NH$_4$)$^+$; 400.2(M+Na)$^+$

We claim:

1. A compound of formula wherein
R$^1$ is an acyl group selected from a. R$^{10}$—C(O)—
b. R$^{11}$—(CH$_2$)$_j$—C(O)—
c. R$^{11}$—CH(R$^{12}$)—C(O)—
d. R$^{11}$—CH$_2$—O—C(O)—
e. R$^{11}$—O—CH$_2$—C(O)—
f. R$^{11}$—S—CH$_2$—C(O)—
g. R$^{11}$—C(=NOR$^3$)—C(O)—

R$^2$ is hydrogen, hydroxy, lower alkyl, cycloalkyl, lower alkoxy, lower alkenyl, cycloalkenyl, lower alkynyl, benzyl, phenoxy, benzyloxy, aryl selected from phenyl, tolyl, xylyl, mesityl, cumenyl, naphthyl, anthryl, phenanthyl, or a heterocyclic ring selected from pyridyl, pyrazinyl, piperidyl, piperidino, N-oxido-pyridyl, pyrimidyl, piperazinyl, pyrrolidinyl, pyridazinyl, N-oxide-pyridazinyl, pyrazolyl, triazinyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,25-oxadiazolyl, 1,23-triazolyl, 1,2,4-triazolyl, 1H-tetrazolyl, 2H-tetrazolyl, thienyl, furyl, hexamethyleneiminyl, oxepanyl, 1H-azepinyl, thiophenyl, tetrahydrothiophenyl, 3H-1,2,3-oxathiazolyl, 1,2,3-oxadiazolyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, oxazolidinyl, and tetrahydrothienyl; the lower alkyl, cycloalkyl, lower alkoxy, lower alkenyl, cycloalkenyl, lower alkynyl, aryl, benzyl, phenoxy, benzyloxy and the heterocyclic ring being unsubstituted or substituted with at least one group selected from carboxy, amino, nitro, cyano, lower alkyl, lower alkoxy, hydroxy, halogen, —CONR$^{21}$R$^{22}$, —N(R$^{22}$)COOR$^{23}$, R$^{22}$CO—, R$^{22}$OCO or R$^{22}$COO—, wherein R$^{21}$ is hydrogen, lower alkyl, or cycloalkyl; R$^{22}$ is hydrogen or lower alkyl; R$^{23}$ is lower alkyl, lower alkenyl or a carboxylic acid protecting group;

j is 0, 1, 2 or 3;

R$^3$ is hydrogen, lower alkyl, cycloalkyl, carbamoyl-lower alkyl, or benzyl;

R$^{10}$ is hydrogen, lower alkyl, cycloalkyl, lower alkoxy, lower alkenyl or cycloalkenyl, the lower alkyl group or the lower alkenyl group being optionally substituted with at least one group selected from halogen, cyano, nitro, amino, mercapto, alkylthio or cyano-methylthio;

R$^{11}$ is aryl selected from phenyl, tolyl, xylyl, mesityl, cumenyl, naphthyl, anthryl, phenanthyl which is unsubstituted or substituted with at least one group selected from halogen, hydroxy, nitro, amino, cyano, carboxy, lower alkyl, lower alkoxy, carbamoyl, trifluoromethyl or aminomethyl; a heterocyclic ring selected from pyridyl, pyrazinyl, piperidyl, piperidino, N-oxido-pyridyl, pyrimidyl, piperazinyl, pyrrolidinyl, pyridazinyl, N-oxide-pyridazinyl, pyrazolyl, triazinyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl, thienyl, furyl, hexamethyleneiminyl, oxepanyl, 1H-azepinyl, thiophenyl, tetrahydrothiophenyl, 3H-1,2,3-oxathiazolyl, 1,2,3-oxadiazolyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, oxazolidinyl, and tetrahydrothienyl; which is unsubstituted or substituted with at least one group selected from halogen, hydroxy, nitro, amino, cyano, carboxy, lower alkyl, lower alkoxy, carbamoyl, trifluoromethyl, aminomethyl or substituted with optionally substituted phenyl or fused together with a benzene ring;

R$^{12}$ is amino, acylamino, hydroxy, sulfato, a carboxyl salt, protected carboxy or azido, as well as readily hydrolyzable esters thereof, pharmaceutically acceptable salts of said compounds and hydrates of the compounds of formula I and of their esters and salts.

2. The compound of claim 1 with the 3-substituent in the E-form, having the formula Ia

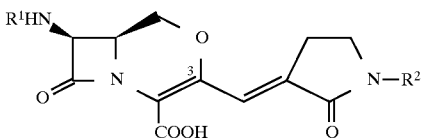

3. The compound of claim 1 with the 3-substituent in the Z-form, having the formula Ib

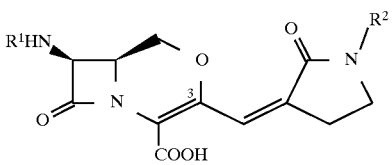

4. The compound of claim 1, wherein $R^1$ is formula a.
5. The compound of claim 4, wherein $R^1$ is acetyl.
6. The compound of claim 1, wherein $R^1$ is formula b.
7. The compound of claim 6, wherein $R^1$ is 2,6-dichlorophenyl-5-methylisoxazol-4-yl-carbonyl.
8. The compound of claim 1, wherein $R^1$ is formula f.
9. The compound of claim 8, wherein $R^1$ is 1-methyl-tetrazol-5-yl-sulfanyl-acetyl.
10. The compound of claim 1, wherein $R^1$ is formula g.
11. The compound of claim 10, having the formula II

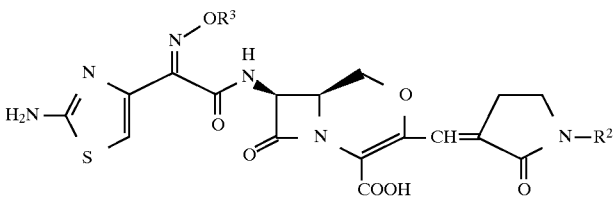

12. The compound of claim 11, wherein $R^3$ is hydrogen, carbamoyl-lower alkyl or cycloalkyl.
13. The compound of claim 12, wherein $R^3$ is hydrogen, carbamoylmethyl, or cyclopentyl.
14. The compound of claim 13, wherein $R^3$ is cyclopentyl.
15. The compound of claim 14, wherein $R^2$ is lower alkyl, cycloalkyl, benzyl, aryl selected from phenyl, tolyl, xylyl, mesityl, cumenyl, naphthyl, anthryl, phenanthryl or a heterocyclic ring selected from pyridyl, pyrazinyl, piperidyl, piperidino, N-oxido-pyridyl, pyrimidyl, piperazinyl, pyrrolidinyl, pyridazinyl, N-oxide-pyridazinyl, pyrazolyl, triazinyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl, thienyl, furyl, hexamethyleneiminyl, oxepanyl, 1H-azepinyl, thiophenyl, tetrahydrothiophenyl, 3H-1,2,3-oxathiazolyl, 1,2,3-oxadiazolyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, oxazolidinyl, and tetrahydrothienyl, the lower alkyl, aryl-lower alkyl, aryl and heterocyclic ring being unsubstituted or substituted with at least one group selected from halogen, hydroxy, amino, nitro, cyano, lower alkyl, lower alkoxy.
16. The compound of claim 15, wherein $R^2$ is isobutyl, 2,2,2-trifluoroethyl, cyclopropyl, phenyl, 3-nitrophenyl, 4-hydroxyphenyl, 2-fluorophenyl, 2-methoxyphenyl, 4-nitrobenzyl, pyridinyl, N-methyl-pyridinium-2-yl or 5-methyl-isoxazolyl.
17. The compound of claim 16, (E)-(6S,7S)-7-[(Z)-2-(2-Amino-thiazol-4-yl)-2-cyclopentyloxyimino-acetylamino]-8-oxo-3-[(E)-2-oxo-1-(2,2,2-trifluoro-ethyl)-pyrrolidin-3-ylidenmethyl]-4-oxa-1-aza-bicyclo[4.2.0.] oct-2-ene-2-carboxylic acid sodium salt.
18. The compound of claim 16, (E)-(6S,7S)-7-[(Z)-2-(2-Amino-thiazol-4-yl)-2-cyclopentyloxyimino-acetylamino]-8-oxo-3-[(E)-2-oxo-1-phenyl-pyrrolidin-3-ylidenmethyl]-4-oxa-1-aza-bicyclo[4.2.0.] oct-2-ene-2-carboxylic acid sodium salt.
19. The compound of claim 16, (E)-(6S,7S)-7-[(Z)-2-(2-Amino-thiazol-4-yl)-2-cyclopentyloxyimino-acetylamino]-8-oxo-3-[(E)-1-(4-nitro-benzyl)-2-oxo-pyrrolidin-3-ylidenemethyl]-4-oxa-1-aza-bicyclo[4.2.0.] oct-2-ene-2-carboxylic acid sodium salt.
20. The compound of claim 16, (E)-(6S,7S)-7-[(Z)-2-(2-Amino-thiazol-4-yl)-2-cyclopentyloxyimino-acetylamino]-8-oxo-3-[(E)-1-(cyclopropyl)-2-oxo-pyrrolidin-3-ylidenemethyl]-4-oxa-1-aza-bicyclo[4.2.0.] oct-2-ene-2-carboxylic acid sodium salt.
21. The compound of claim 16, (E)-(6S,7S)-7-[(Z)-2-(2-Amino-thiazol-4-yl)-2-cyclopentyloxyimino-acetylamino]-8-oxo-3-[(E)-1-(isobutyl)-2-oxo-pyrrolidin-3-ylidenemethyl]-4-oxa-1-aza-bicyclo[4.2.0.] oct-2-ene-2-carboxylic acid sodium salt.
22. The compound of claim 16, (E)-(6S,7S)-7-[(Z)-2-(2-Amino-thiazol-4-yl)-2-cyclopentyloxyimino-acetylamino)-8-oxo-3-[(E)-1-(5-methyl-isooxazolyl)-2-oxo-pyrrolidin-3-ylidenemethyl]-4-oxa-1-aza-bicyclo[4.2.0.] oct-2-ene-2-carboxylic acid sodium salt.
23. The compound of claim 16, (E)-(6S,7S)-7-[(Z)-2-(2-Amino-thiazol-4-yl)-2-cyclopentyloxyimino-acetylamino]-8-oxo-3-[(E)-1-(3-nitrophenyl)-2-oxo-pyrrolidin-3-ylidenemethyl]-4-oxa-1-aza-bicyclo [4.2.0.] oct-2-ene-2-carboxylic acid sodium salt.
24. The compound of claim 16, (E)-(6S,7S)-7-[(Z)-2-(2-Amino-thiazol-4-yl)-2-cyclopentyloxyimino-acetylamino]-8-oxo-3-[(E)-1-(4-hydroxyphenyl)-2-oxo-pyrrolidin-3-ylidenemethyl]-4-oxa-1-aza-bicyclo[4.2.0.] oct-2-ene-2-carboxylic acid sodium salt.
25. The compound of claim 16, (E)-(6S,7S)-7-[(Z)-2-(2-Amino-thiazol-4-yl)-2-cyclopentyloxyimino-acetylamino]-3-[(E)-1-(2-fluoro-phenyl)-2-oxo-pyrrolidin-3-ylidenemethyl]-8-oxo-4-oxa-1-aza-bicyclo[4.2.0.] oct-2-ene-2-carboxylic acid sodium salt.
26. The compound of claim 16, (E)-(6S,7S)-7-[(Z)-2-(2-Amino-thiazol-4-yl)-2-cyclopentyloxyimino-acetylamino]-3-[2-oxo-1-(2-pyridinyl)-pyrrolidin- 3-ylidenemethyl]-8-oxo-4-oxa-1-aza-bicyclo[4.2.0.] oct-2-ene-2-carboxylic acid sodium salt.

27. The compound of claim 16, (E)-(6S,7S)-7-[(Z)-2-(2-Amino-thiazol-4-yl)-2-cyclopentyloxyimino-acetylamino]-3-[(E)-1-(1-methyl-pyridinium-2-yl)-2-oxo-pyrrolidin-3-ylidenemethyl]-8-oxo-4-oxa-1-aza-bicyclo[4.2.0.] oct-2-ene-2-carboxylic acid.

28. The compound of claim 16, (E)-(6S,7S)-7-[(Z)-2-(2-Amino-thiazol-4-yl)-2-cyclopentyloxyimino-acetylamino]-3-[1-(2-methoxy-phenyl)-2-oxo-pyrrolidin-3-ylidenemethyl]-8-oxo-4-oxa-1-aza-bicyclo[4.2.0.] oct-2-ene-2-carboxylic acid sodium salt.

29. The compound of claim 13, wherein $R^3$ is carbamoylmethyl.

30. The compound of claim 29, wherein $R^2$ is lower alkyl, cycloalkyl, benzyl, aryl selected from phenyl, tolyl, xylyl, mesityl, cumenyl, naphthyl, anthryl, phenanthryl or a heterocyclic ring selected from pyridyl, pyrazinyl, piperidyl, piperidino, N-oxido-pyridyl, pyrimidyl, piperazinyl, pyrrolidinyl, pyridazinyl, N-oxide-pyridazinyl, pyrazolyl, triazinyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl, thienyl, furyl, hexamethyleneiminyl, oxepanyl, 1H-azepinyl, thiophenyl, tetrahydrothiophenyl, 3H-1,2,3-oxathiazolyl, 1,2,3-oxadiazolyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, oxazolidinyl, and tetrahydrothienyl, the lower alkyl, aryl-lower alkyl, aryl and heterocyclic ring being unsubstituted or substituted with at least one group selected from halogen, hydroxy, amino, nitro, cyano, lower alkyl, lower alkoxy.

31. The compound of claim 30, wherein $R^2$ is isobutyl, 2,2,2-trifluoroethyl, cyclopropyl, phenyl, 3-nitrophenyl, 4-hydroxyphenyl, 2-fluorophenyl, 2-methoxyphenyl, 4-nitrobenzyl, pyridinyl, N-methyl-pyridinium-2-yl or 5-methyl-isoxazolyl.

32. The compound of claim 30, (E)-(6S,7S)-7-[(Z)-2-(2-Amino-thiazol-4-yl)-2-carbamoylmethoxyimino-acetylamino]-3-[(E)-1-(4-nitro-benzyl)-2-oxo-pyrrolidin-3-ylidenemethyl]-8-oxo-4-oxa-1-aza-bicyclo[4.2.0.] oct-2-ene-2-carboxylic acid sodium salt.

33. The compound of claim 31, (E)-(6S,7S)-7-[(Z)-2-(2-Amino-thiazol-4-yl)-2-carbamoylmethoxyimino-acetylamino]-3-[(E)-1-(phenyl)-2-oxo-pyrrolidin-3-ylidenemethyl]-8-oxo-4-oxa-1-aza-bicyclo[4.2.0.] oct-2-ene-2-carboxylic acid sodium salt.

34. The compound of claim 31, (E)-(6S,7S)-7-[(Z)-2-(2-Amino-thiazol-4-yl)-2-carbamoylmethoxyimino-acetylamino]-3-[(E)-1-cyclopropyl- 2-oxo-pyrrolidin-3-ylidenemethyl]-8-oxo-4-oxa-1-aza-bicyclo[4.2.0.] oct-2-ene-2-carboxylic acid sodium salt.

35. The compound of claim 31, (E)-(6S,7S)-7-[(Z)-2-(2-Amino-thiazol-4-yl)-2-carbamoylmethoxyimino-acetylamino]-3-[(E)-1-(5-methyl-isooxazolyl)-2-oxo-pyrrolidin-3-ylidenemethyl]-8-oxo-4-oxa-1-aza-bicyclo[4.2.0.] oct-2-ene-2-carboxylic acid sodium salt.

36. The compound of claim 31, (E)-(6S,7S)-7-[(Z)-2-(2-Amino-thiazol-4-yl)-2-carbamoylmethoxyimino-acetylamino]-3-[(E)-1-isobutyl-2-oxo-pyrrolidin-3-ylidenemethyl]-8-oxo-4-oxa-1-aza-bicyclo[4.2.0.] oct-2-ene-2-carboxylic acid sodium salt.

37. The compound of claim 31, (E)-(6S,7S)-7-[(Z)-2-(2-Amino-thiazol-4-yl)-2-carbamoylmethoxyimino-acetylamino]-3-[(E)-1-(3-nitrophenyl)-2-oxo-pyrrolidin-3-ylidenemethyl]-8-oxo-4-oxa-1-aza-bicyclo[4.2.0.] oct-2-ene-2-carboxylic acid sodium salt.

38. The compound of claim 13, wherein $R^3$ is hydrogen.

39. The compound of claim 38, wherein $R^2$ is lower alkyl, cycloalkyl, benzyl, aryl selected from phenyl, tolyl, xylyl, mesityl, cumenyl, naphthyl, anthryl, phenanthryl or a heterocyclic ring selected from pyridyl, pyrazinyl, piperidyl, piperidino, N-oxido-pyridyl, pyrimidyl, piperazinyl, pyrrolidinyl, pyridazinyl, N-oxide-pyridazinyl, pyrazolyl, triazinyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl, thienyl, furyl, hexamethyleneiminyl, oxepanyl, 1H-azepinyl, thiophenyl, tetrahydrothiophenyl, 3H-1,2,3-oxathiazolyl, 1,2,3-oxadiazolyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, oxazolidinyl, and tetrahydrothienyl, the lower alkyl, aryl-lower alkyl, aryl and heterocyclic ring being unsubstituted or substituted with at least one group selected from halogen, hydroxy, amino, nitro, cyano, lower alkyl, lower alkoxy.

40. The compound of claim 39, wherein $R^2$ is isobutyl, 2,2,2-trifluoroethyl, cyclopropyl, phenyl, 3-nitrophenyl, 4-hydroxyphenyl, 2-fluorophenyl, 2-methoxyphenyl, 4-nitrobenzyl, pyridinyl, N-methyl-pyridinium-2-yl or 5-methyl-isoxazolyl.

41. The compound of claim 40, (E)-(6S,7S)-7-[(Z)-2-(2-Amino-thiazol-4-yl)-2-hydroxyimino-acetylamino]-8-oxo-3-[(E)-1-(2-methoxy-phenyl)-2-oxo-pyrrolidin-3-ylidenemethyl]-4-oxa-1-aza-bicyclo[4.2.0.] oct-2-ene-2-carboxylic acid sodium salt.

42. The compound of claim 40, (E)-(6S,7S)-7-[(Z)-2-(2-Amino-thiazol-4-yl)-2-hydroxyimino-acetylamino]-8-oxo-3-[(E)-1-(isobutyl)-2-oxo-pyrrolidin- 3-ylidenemethyl]-4-oxa-1-aza-bicyclo[4.2.0.] oct-2-ene-2-carboxylic acid sodium salt.

43. The compound of claim 40, (E)-(6S,7S)-7-[(Z)-2-(2-Amino-thiazol-4-yl)-2-hydroxyimino-acetylamino]-8-oxo-3-[(E)-1-(2-fluoro-phenyl)-2-oxo-pyrrolidin-3-ylidenemethyl]-4-oxa-1-aza-bicyclo[4.2.0.] oct-2-ene-2-carboxylic acid sodium salt.

44. The compound of claim 40, (E)-(6S,7S)-7-[(Z)-2-(2-Amino-thiazol-4-yl)-2-hydroxyimino-acetylamino]-8-oxo-3-[(E)-1-(3-nitro-phenyl)-2-oxo-pyrrolidin-3-ylidenemethyl]-4-oxa-1-aza-bicyclo[4.2.0.] oct-2-ene-2-carboxylic acid sodium salt.

45. The compound of claim 40, (E)-(6S,7S)-7-[(Z)-2-(2-Amino-thiazol-4-yl)-2-hydroxyimino-acetylamino]-8-oxo-3-[(E)-1-(pyridin-2-yl)-2-oxo-pyrrolidin-3-ylidenemethyl]-4-oxa-1-aza-bicyclo[4.2.0.] oct-2-ene-2-carboxylic acid sodium salt.

46. The compound of claim 40, E)-(6S,7S)-7-[(Z)-2-(2-Amino-thiazol-4-yl)-2-hydroxyimino-acetylamino]-8-oxo-3-[(E)-1-(4-nitro-benzyl)-2-oxo-pyrrolidin-3-ylidenemethyl]-4-oxa-1-aza-bicyclo[4.2.0.] oct-2-ene-2-carboxylic acid sodium salt.

47. The compound of claim 40, (E)-(6S,7S)-7-[(Z)-2-(2-Amino-thiazol-4-yl)-2-hydroxyimino-acetylamino]-8-oxo-3-[(E)-1-(5-methyl-isooxazolyl)-2-oxo-pyrrolidin-3-ylidenemethyl]-4-oxa-1-aza-bicyclo[4.2.0.] oct-2-ene-2-carboxylic acid sodium salt.

48. The compound of claim 7, (E)-(6S,7S)-7-[[3-(2,6-Dichloro-phenyl)-5-methyl-isoxazol-4-yl-carbonyl]-amino]-3-[(E)-1-(isobutyl)-2-oxo-pyrrolidin-3-ylidenemethyl]-4-oxa-1-aza-bicyclo[4.2.0.] oct-2-ene-2-carboxylic acid sodium salt.

49. The compound of claim 9, (6S,7S)-3-((E)-1-Isobutyl-2-oxo-pyrrolidin-3-ylidenemethyl)-7 [2-(1-methyl-1H-tetrazol-5-ylsulfanyl)-acetylamino)-8-oxo-4-oxa-1-aza-bicyclo[4.2.0.] oct-2-ene-2-carboxylic acid sodium salt.

50. The compound of claim 5, (6S,7S)-7-Acetylamino-3-((E)-1-isobutyl-2-oxo-pyrrolidin-3-ylidenemethyl)-8-oxo-4-oxa-1-aza-bicyclo[4.2.0.] oct-2-ene-2-carboxylic acid sodium salt.

51. A pharmaceutical composition comprising a compound of formula I

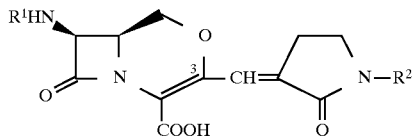

wherein $R^1$ is an acyl group selected from

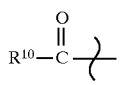 a

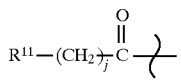 b

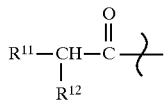 c

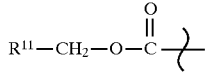 d

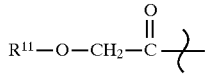 e

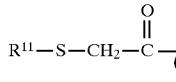 f

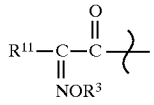 g $R^2$ is hydrogen, hydroxy, lower alkyl, cycloalkyl, lower alkoxy, lower alkenyl, cycloalkenyl, lower alkynyl, benzyl, phenoxy, benzyloxy, aryl selected from phenyl, tolyl, xylyl, mesityl, cumenyl, naphthyl, anthryl, phenanthyl, or a heterocyclic ring selected from pyridyl, pyrazinyl, piperidyl, piperidino, N-oxido-pyridyl, pyrimidyl, piperazinyl, pyrrolidinyl, pyridazinyl, N-oxide-pyridazinyl, pyrazolyl, triazinyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl, thienyl, furyl, hexamethyleneiminyl, oxepanyl, 1H-azepinyl, thiophenyl, tetrahydrothiophenyl, 3H-1,2,3-oxathiazolyl, 1,2,3-oxadiazolyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, oxazolidinyl, and tetrahydrothienyl; the lower alkyl, cycloalkyl, lower alkoxy, lower alkenyl, cycloalkenyl, lower alkynyl, aryl, benzyl, phenoxy, benzyloxy and the heterocyclic ring being unsubstituted or substituted with at least one group selected from carboxy, amino, nitro, cyano, lower alkyl, lower alkoxy, hydroxy, halogen, $-CONR^{21}R^{22}$, $-N(R^{22})COOR^{23}$, $R^{22}CO-$, $R^{22}OCO$ or $R^{22}COO-$, wherein $R^{21}$ is hydrogen, lower alkyl, or cycloalkyl; $R^{22}$ is hydrogen or lower alkyl; $R^{23}$ is lower alkyl, lower alkenyl or a carboxylic acid protecting group;

j is 0, 1, 2 or 3;

$R^3$ is hydrogen, lower alkyl, cycloalkyl, carbamoyl-lower alkyl, or benzyl;

$R^{10}$ is hydrogen, lower alkyl, cycloalkyl, lower alkoxy, lower alkenyl or cycloalkenyl, the lower alkyl group or the lower alkenyl group being optionally substituted with at least one group selected from halogen, cyano, nitro, amino, mercapto, alkylthio or cyano-methylthio;

$R^{11}$ is aryl selected from phenyl, tolyl, xylyl, mesityl, cumenyl, naphthyl, anthryl, phenanthyl which is unsubstituted or substituted with at least one group selected from halogen, hydroxy, nitro, amino, cyano, carboxy, lower alkyl, lower alkoxy, carbamoyl, trifluoromethyl or aminomethyl; a heterocyclic ring selected from pyridyl, pyrazinyl, piperidyl, piperidino, N-oxido-pyridyl, pyrimidyl, piperazinyl, pyrrolidinyl, pyridazinyl, N-oxide-pyridazinyl, pyrazolyl, triazinyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl, thienyl, furyl, hexamethyleneiminyl, oxepanyl, 1H-azepinyl, thiophenyl, tetrahydrothiophenyl, 3H-1,2,3-oxathiazolyl, 1,2,3-oxadiazolyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, oxazolidinyl, and tetrahydrothienyl; which is unsubstituted or substituted with at least one group selected from halogen, hydroxy, nitro, amino, cyano, carboxy, lower alkyl, lower alkoxy, carbamoyl, trifluoromethyl, aminomethyl or substituted with optionally substituted phenyl or fused together with a benzene ring;

$R^{12}$ is amino, acylamino, hydroxy, sulfato, a carboxyl salt, protected carboxy or azido, as well as readily hydrolyzable esters thereof, pharmaceutically acceptable salts of said compounds and hydrates of the compounds of formula I and of their esters and salts; and a pharmaceutically acceptable carrier.

52. A method treating infectious diseases caused by *S.aureus*, *E.faecalis*, *E.faecium*, *E.coli*, and *E.cloacae* in a host comprising administering to said host in need of such treatment a therapeutically effective amount of a compound of formula I

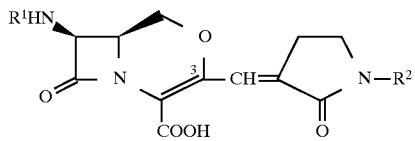

wherein $R^1$ is an acyl group selected from

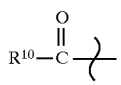 a

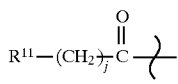 b

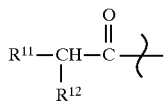 c

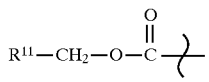 d

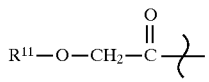 e

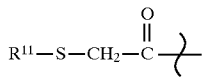 f

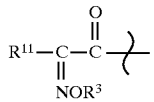 g $R^2$ is hydrogen, hydroxy, lower alkyl, cycloalkyl, lower alkoxy, lower alkenyl, cycloalkenyl, lower alkynyl, benzyl, phenoxy, benzyloxy, aryl selected from phenyl, tolyl, xylyl, mesityl, cumenyl, naphthyl, anthryl, phenanthyl, or a heterocyclic ring selected from pyridyl, pyrazinyl, piperidyl, piperidino, N-oxido-pyridyl, pyrimidyl, piperazinyl, pyrrolidinyl, pyridazinyl, N-oxide-pyridazinyl, pyrazolyl, triazinyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,25-oxadiazolyl, 1,23-triazolyl, 1,2,4-triazolyl, 1H-tetrazolyl, 2H-tetrazolyl, thienyl, furyl, hexamethyleneiminyl, oxepanyl, 1H-azepinyl, thiophenyl, tetrahydrothiophenyl, 3H-1,2,3-oxathiazolyl, 1,2,3-oxadiazolyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, oxazolidinyl, and tetrahydrothienyl; the lower alkyl, cycloalkyl, lower alkoxy, lower alkenyl, cycloalkenyl, lower alkynyl, aryl, benzyl, phenoxy, benzyloxy and the heterocyclic ring being unsubstituted or substituted with at least one group selected from carboxy, amino, nitro, cyano, lower alkyl, lower alkoxy, hydroxy, halogen, —$CONR^{21}R^{22}$, —$N(R^{22})COOR^{23}$, $R^{22}CO$—, $R^{22}OCO$ or $R^{22}COO$—, wherein $R^{21}$ is hydrogen, lower alkyl, or cycloalkyl; $R^{22}$ is hydrogen or lower alkyl; $R^{23}$ is lower alkyl, lower alkenyl or a carboxylic acid protecting group;

j is 0, 1, 2 or 3;

$R^3$ is hydrogen, lower alkyl, cycloalkyl, carbamoyl-lower alkyl, or benzyl;

$R^{10}$ is hydrogen, lower alkyl, cycloalkyl, lower alkoxy, lower alkenyl or cycloalkenyl, the lower alkyl group or the lower alkenyl group being optionally substituted with at least one group selected from halogen, cyano, nitro, amino, mercapto, alkylthio o r cyano-methylthio;

$R^{11}$ is aryl selected from phenyl, tolyl, xylyl, mesityl, cumenyl, naphthyl, anthryl, phenanthyl which is unsubstituted or substituted with at least one group selected from halogen, hydroxy, nitro, amino, cyano, carboxy, lower alkyl, lower alkoxy, carbamoyl, trifluoromethyl or aminomethyl; a heterocyclic ring selected from pyridyl, pyrazinyl, piperidyl, piperidino, N-oxido-pyridyl, pyrimidyl, piperazinyl, pyrrolidinyl, pyridazinyl, N-oxide-pyridazinyl, pyrazolyl, triazinyl, imidazolyl, thiazolyl, 1,2,3-thiadiazolyl, 1,2, 4thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl, thienyl, furyl, hexamethyleneiminyl, oxepanyl, 1H-azepinyl, thiophenyl, tetrahydrothiophenyl, 3H-1,2,3-oxathiazolyl, 1,2,3-oxadiazolyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, oxazolidinyl, and tetrahydrothienyl; which is unsubstituted or substituted with at least one group selected from halogen, hydroxy, nitro, amino, cyano, carboxy, lower alkyl, lower alkoxy, carbamoyl, trifluoromethyl, aminomethyl or substituted with optionally substituted phenyl or fused together with a benzene ring;

$R^{12}$ is amino, acylamino, hydroxy, sulfato, a carboxyl salt, protected carboxy or azido, as well as readily hydrolyzable esters thereof, pharmaceutically acceptable salts of said compounds and hydrates of the compounds of formula I and of their esters and salts.

* * * * *

UNITED STATES PATENT AND TRADEMARK OFFICE
CERTIFICATE OF CORRECTION

PATENT NO. : 5,811,419
DATED : September 22, 1998
INVENTOR(S) : Christian Hubschwerlen and Jean-Luc Specklin It is certified that error appears in the above-identified patent and that said Letters Patent is hereby corrected as shown below:

Column 55, Claim 32, line 40, delete "claim 30," and insert -- claim 31, --.

Column 60, Claim 52, line 34, delete "4thiadiazolyl," and insert -- 4-thiadiazolyl, --.

Signed and Sealed this

Sixteenth Day of February, 1999

Attest:

*Acting Commissioner of Patents and Trademarks*

*Attesting Officer*